US008252062B2

United States Patent
Bandoh et al.

(10) Patent No.: US 8,252,062 B2
(45) Date of Patent: Aug. 28, 2012

(54) ARTIFICIAL CEMENTLESS HIP PROSTHESIS STEM

(75) Inventors: Sunichi Bandoh, Kakamigahara (JP); Masaru Zako, Takatsuki (JP); Nobuhiko Sugano, Suita (JP)

(73) Assignee: Kabushiki Kaisha B.I. Tec, Gifu (JP)

( * ) Notice: Subject to any disclaimer, the term of this patent is extended or adjusted under 35 U.S.C. 154(b) by 456 days.

(21) Appl. No.: 12/095,251

(22) PCT Filed: Nov. 28, 2006

(86) PCT No.: PCT/JP2006/323724
§ 371 (c)(1),
(2), (4) Date: Aug. 31, 2010

(87) PCT Pub. No.: WO2007/063853
PCT Pub. Date: Jun. 7, 2007

(65) Prior Publication Data
US 2010/0312354 A1 Dec. 9, 2010

(30) Foreign Application Priority Data
Nov. 30, 2005 (JP) .................................. 2005-345097

(51) Int. Cl.
*A61F 2/32* (2006.01)
(52) U.S. Cl. ................ 623/23.32; 623/23.17; 623/23.18; 623/23.19
(58) Field of Classification Search .... 623/23.17–23.19, 623/23.21, 23.29, 23.32–23.34
See application file for complete search history.

(56) References Cited

U.S. PATENT DOCUMENTS

| 4,750,905 A * | 6/1988 | Koeneman et al. ........ 623/23.51 |
| 5,181,930 A * | 1/1993 | Dumbleton et al. ....... 623/23.34 |
| 5,314,492 A * | 5/1994 | Hamilton et al. .......... 623/23.34 |
| 5,389,107 A * | 2/1995 | Nassar et al. .............. 623/23.17 |
| 6,602,293 B1 * | 8/2003 | Biermann et al. .......... 623/23.5 |
| 6,676,704 B1 * | 1/2004 | Pope et al. ................. 623/18.11 |

FOREIGN PATENT DOCUMENTS
GB 2423025 A * 8/2006
WO WO 2005034818 A1 * 4/2005
* cited by examiner

*Primary Examiner* — Corrine M McDermott
*Assistant Examiner* — Randy Shay
(74) *Attorney, Agent, or Firm* — William J. Sapone; Coleman Sudol Sapone P.C.

(57) ABSTRACT

An artificial cement-less hip prosthesis stem comprises an inner construct 7 which reacts with a load acting on a hip joint and an outer construct 8 for transmitting the load acting on the inner construct to a femur 1. The inner construct has an inner body 7B which reacts with the load transmitted from a neck 7A. The outer construct has both an outer body 8A which is bell mouth-shaped toward an epiphysis so as to surround the inner body 7B and a leg 8B extending toward a medullary cavity. The torsional rigidity given to the proximal end and the distal end of the outer body 8A and the leg 8B is regulated so as to be lower than the torsional rigidity given to an intermediate portion 18 of the outer body 8A.

20 Claims, 16 Drawing Sheets

PRIOR ART

ARTIFICIAL CEMENTLESS HIP PROSTHESIS STEM

TECHNICAL FIELD

The present invention relates to an artificial cement-less hip prosthesis stem, more particularly, to a stem made of composite material, which can reduce an unfavorable load acted on a femur not only by eliminating the concentration of shearing stress occurring at both the proximal end and the distal end of the interface between the stem and the femur, but also by transmitting the load charged on the hip prosthesis through the proximal portion as well as in a normal state.

BACKGROUND ART

As shown in FIG. 13, a hip joint in which a pelvis 61 is connected with a femur 62 by a caput 63 which works as a spherical bearing, enables the movements such as uprightly standing, walking, sitting-down and the like. The femur 62 has a greater trochanter and lesser trochanter at the proximal portion thereof, and gluteus medius 65 connected with the greater trochanter 64 at the epiphysis controls movements of the femur. The break of spherical bearing due to an accident or the like loses the cooperation of the femur 62 and the pelvis 61 so that the leg comes to be uncontrollable and is not able to support the ordinary daily life.

The reproduction of the spherical bearing and the introduction of the supporting mechanism thereof are required in order to recover the function of the hip joint. The spherical bearing, not illustrated in the figure, consists of a socket fixed to the pelvis and a spherical head which cooperates with the socket so as to operate as an articulation, the supporting mechanism is a stem which supports the spherical head to transmit the load to the femur. The socket and spherical head are required high wearability and durability enough to be used as a bearing. Recently, the development of the material thereof has been remarkably advanced as well as the performance thereof has been greatly improved, so it seems that the technology of the spherical bearing has just been grown up.

The stem is a short rod 66, as shown in FIG. 13 (b), which is implanted into the femur 62, being inserted into a deep hollow 67 extending from the epiphysis to the diaphysis so as not to pass through the greater trochanter 64. As shown in FIG. 13 (c), the deep hollow is formed by excising some spongiosa 69 and a part of medulla in the cortical bone 68 having high stiffness by means of a medical rasp, so as to have the depth reaching to medullary cavity 70. The stem 66 consists of a neck 66a for introducing a load from the spherical head 71, of a body part 66b for supporting the neck and transmitting the load to the femur, and of a leg 66c for guiding the insertion of the stem into the hollow and keeping the attitude thereof while advancing, as shown in FIG. 13 (d).

A stem ought to be chemically stable, harmless in human bodies, durable, and transmit a load to a femur effectively. It is often made of cobalt alloy and titanium ally and is generally formed axial unsymmetrical, whose external surface is often close to the cortical bone in order to ensure the load transmission, for the body part 66b has to be provided with a shoulder 66d in the epiphysis 72 where there is an unremovable greater trochanter 64, as shown in FIG. 13 (c). FIG. 14 (a) is the graphic arts of the stem 66, and (b) shows a femoral prosthesis while the spherical head 71 is engaged with the stem, however, such a complex shaped stem made of the hard metal mentioned above has made the manufacturing cost very expensive.

It is impossible to excavate a deep hollow that agrees perfectly with a ready-made stem in the femur which is different in every patient. Therefore, a method for uniting the stem with the femur by the cement filled in an oversized deep hollow formed in the femur is adopted, or a method where the stem is tightly inserted into an undersized hollow to unite with the femur by Bone-Growth is adopted. Of course, the shape and the stiffness of the femur are considered for every patient in both methods. The former requires less time for uniting them than the latter does, but un-reacted monomer may lixiviate from the cement, and taking off the stem from the femur is very hard during the re-operation, furthermore, there is a high possibility of suffering from pulmonary embolism, so that recently the latter method has also been researched well to develop the artificial hip prosthesis stem.

The load acted on the hip joint is transmitted as a shearing stress occurring on the interface between the stem and the femur. The shearing stress in the longitudinal direction and the rotational direction has to be evaluated with high accuracy and both the shearing stress and the distribution thereof on the interface have to be corresponding to transmitted load required. Even if the integrated value of the stress acted on the interface agrees with the transmitted load, the stress concentration occurring locally on the interface causes damage of bone and/or sharp pain to patients in the case that the stress is larger than the allowable strength of the surface corresponding thereto. The phenomenon described below will be helpful to understand it.

FIG. 15 (a) shows a modeling of the stem and the femur, wherein the stem is regarded as an inner cylinder 66A and the femur as an outer cylinder 62A. The modelings of (b) and (c) of FIG. 15 show the state where the stem is inserted tightly into the deep hollow of the femur. Although the interface 73 is depicted to be thicker than the actual interface, following phenomena will occur in an actual thin interface. (b) is an example where either compression or tension acts in the vertical direction. When both of the outer cylinder 62A and inner cylinder 66A are isotropic, the shearing stress is concentrated on the both ends 73e of the interface 73, as shown by the distribution of many straight lines of which length is corresponding to the magnitude of stress. The straight lines are drawn by the radial straight lines so as to be clear to see though they should be drawn in the axial direction.

FIG. 15(c) is the example where the torsion is acted on the both cylinders and the torsional shearing stress is concentrated on the both ends as well. Both cases of (b) and (c) teach us that no stress concentration, little fluctuation of stress and extremely low stress occur on the intermediate portion. If the end of interface of the deep hollow cannot withstand the load under such a distribution, it means that the stem cannot be applied to a patient in spite of the fact that the overload is not charged on him. The fact that the shearing stress occurring on the interface is distributed like this has already disclosed in a book authored by R. J. Schliekelmann, a Dutch aircraft engineer.

While a human uprightly standing or walking, not only a load in the vertical direction is acted on the hip joint but also bending stress is acted thereon since the caput 63 deviates from the longitudinal axis of the femur 62, as shown in FIG. 13 (a). The bending moment causes the tension on one side of an object and the compression on the other side thereof, so that both the load in the vertical direction and the bending stress fundamentally makes a stress mechanism caused by the shearing stress acted on the interface as shown in FIG. 15(b). The motion during sitting-down makes a stress mechanism caused by the torsional stress as shown in FIG. 15(c).

The thicker the interface becomes, the duller the phenomena of FIG. 15 become. Nevertheless, if a stem made of isotropic material, e.g., titanium alloy, is implanted into a femur, both the compressing and torsional shearing stresses greatly occur at the end of the proximal portion which is close to the heart and at the end of the distal portion which is away from the heart. Most of the load transmitted to the femur is concentrated to the upper end (the end of proximal portion) of the main body and the end of the thin leg (distal portion).

Thereby, the load to be charged on the hip joint is transmitted also to the distal portion, so that the route for transmitting the load comes to be different from that of the load in a normal state. The reduction of the load charged on the proximal portion which is activated under the appropriate load causes Stress-Shielding that makes the cortical bone thinner and the density thereof lower. Besides, if the stem loosens at the proximal portion, Micro-Movement occurs to make the metallic worn powder therefrom, which may be carcinogenic. Since it is not easy that the figure of metallic stem agrees with that of the deep hollow, Fit and Fill, which mean a fitting rate to the wall of a deep hollow and a filling rate in the cross section of a hollow, are not expected to be very high. These phenomena force the femur to be charged by spotty loads on the contacting surface independently of the distribution of load in FIG. 15, causing the destruction of bones and interfacial separation. Moreover, the serious problem on using the metallic stem is the metallic fatigue caused by applying it to the part of movable structure.

In WO2005/034818A1, a composite material stem is disclosed so as to solve the problem of the metallic stem mentioned above. The principal reason why much attention is drawn to the composite material stem is that fiber reinforced plastics are free from fatigue phenomenon. The cited invention is different from the stem having the metallic core covered with fiber reinforced plastics as disclosed in WO93/19699A1 and U.S. Pat. No. 6,749,639 B2. e.g., the whole of stem is made of composite material and the rigidity of the skin thereof is varied in the longitudinal direction, moreover the structure of the stem is epoch-making, wherein even the core of the stem contributes to the control of epidermis of the stem, which is fundamentally different from U.S. Pat. No. 4,892,552 wherein the stem is cut out from the overlaid block although it is made of composite material only. FIG. 16 is a cross sectional view of the complete composite material stem 74 according to the cited invention, wherein it is implanted to the femur 62, having a simple outer shape without shoulder 66d of the metallic stem 66 which is additionally shown by single-dotted chain lines in FIG. 16(a).

FIG. 16 (a) is a cross sectional view of the stem in the femur observed at the front of a human body, and (b) is at the side of the body. A cortical bone 75 is depicted by double-dotted chain lines around the stem 74, but spongiosa is not. It is worthy of notice that the epidermis 77a of the stem is very thin in the diaphysis 76 and the epidermis 77b is thick in the epiphysis 78, so that the rigidity of the stem from the proximal portion toward the distal portion is gradually decreased by changing the thickness of layer of the composite material between the epidermis 77 and the inner epidermis 80 which give a cavity 79 to the core portion of the stem.

The construction which gives such a change of rigidity is realized by changing the number and the direction of layers of reinforced fiber which forms the epidermis. The foaming resin 81 occupies the space surrounded with the inner epidermis 80 and the epidermis 77a, promoting the shape of the whole stem stable. Since the interfacial stress does not occur locally or greatly at the part where the load can not be transmitted due to the low rigidity thereof, the stress concentration at the distal end is avoidable.

Therefore, the stress concentrates inevitably to the proximal portion, so that the route for transmitting the load can be made to be close to that in a normal state. Since the metallic stem mentioned above is isotropic, the rigidity thereof cannot be decreased at both the proximal end and the distal end to the same degree of that of cortical bone, resulting in that the high shearing stress caused by the tension/compression and the torsion can not be checked at both the ends of the stem. Compared with the metallic stem, the composite material stem enables us easily to have measures to check the concentration of the shearing stress.

However, in the case of the composite material stem overlaid with fiber woven cloth and/or uni-directional fiber for reinforcement and the resin as the matrix, the shoulder which the metallic stem always has forces the fiber woven cloth wrinkle so that the laminating work comes to be rather difficult. Therefore, in order not to decrease the molding quality and not to increase the quality unstable, the shape of the stem should be simple without such a sharp curve as the metallic stem shown by the reference number 66 in FIG. 16 (a) has. However, Fit and Fill at the epiphysis will decrease if the stem does not have a shoulder, resulting in increase in the contacting area with the spongiosa having low durability and in requirement of much time and technical skill for inserting the stem into the deep hollow being curved complicatedly.

Also, referring to FIG. 16 (a), in the epiphysis 78, the connecting force at the side of the greater trochanter is low, but epidermis 77B having a high rigidity at the counter side of the greater trochanter i.e., at the medial side, makes the stress concentrate at the proximal end according to the principle of FIG. 15. The break of caput often makes the cortical bone 75B at the medial side weak and the cutting off a part of the cortical bone during the operation makes the strength thereof low, moreover, the cortical bone is charged with the heaviest load when the bending moment acts on the stem by the load charged on the spherical head after the operation. Therefore, the cortical bone 75B is damaged when the stress concentrates on the weakened part, so that it will lose the property to withstand the load, resulting in the failure of the function as an artificial hip joint.

It is very difficult to decrease in the rigidity of epidermis 77 at the epiphysis of the composite material stem, for the epidermis is extended to the neck 66a which supports the spherical head 72 and the cavity 79 cannot be extended till the vicinity of the neck where the rigidity has to be high, consequently, the artificial hip joint of FIG. 16 can not be always applied to the patients of osteoporosis or the like, resulting in the limit of application thereof.

In order to fit a stem to the hollow of a patient femur the shape of the hollow has to be determined according to the data of three-dimensional CT graphics of a femur. The outer shape of epidermis of the stem touching the wall of the hollow has to be formed with high accuracy. The process to form the stem cannot be easily divided, for it consists of single parts, or many complicated processes are required. Not only the pressure control in the mold is difficult but also the miniaturization and lightening of the mold does not progress. Even partially, ready-made stems are not still usable consequently, inexpensive stems are unavailable.

DISCLOSURE OF INVENTION

Problems to be Solved

The object of the present invention is to provide an artificial cement-less hip prosthesis stem in order to solve the problems mentioned above; the first is to eliminate not only the shearing stress concentration occurring at the distal end of a stem but also that at the proximal end thereof so that the load acted on the hip prosthesis is distributed collectively on the same proximal portion as the load is transmitted in a normal state and so that the fluctuation of stress distribution is reduced, the second is to make easily the outer shape of the stem having high Fit and Fill in the deep hollow, the third is to improve the quality of the stem by simplifying the process for making composite material stem so as not to have a complicated shape and the fourth is to realize the low cost of custom-made stems by simplifying and miniaturizing the molds.

Disclosure of Invention

The present invention is applied to the artificial cementless hip prosthesis stem which is implanted into the deep hollow extending from the epiphysis to the diaphysis of the femur so as not to pass through the greater trochanter, gradually united with the femur by Bone-Growth, comprising; referring to FIG. 1, an inner construct 7 reacted with the load acted on the hip joint and an outer construct 8 transmitting the load acted on the inner construct to the femur 1. The former construct has a neck 7A to be engaged with the spherical head 9 which works as a joint in cooperation with a socket fixed to a pelvis, and the inner body 7B to be reacted with the load transmitted from the neck. The latter construct made of fiber reinforced plastics has both the outer body 8B which is bell mouth-shaped toward the epiphysis so as to surround the inner body 7B and the leg 8B combined with the outer body 8A and extending toward the medullary cavity. The adhesive filler 12 is filled in the space between the outer body 8A and the inner body 7B so as to combine with each other. The torsional rigidity given to the proximal end and the distal end of the outer body 8A and the leg 8B is regulated lower than the torsional rigidity given to the intermediate portion 18 of the outer body 8A, resulting in transmitting the load distributed collectively on the intermediate portion to the proximal portion of the femur 1 as uniformly as possible.

The inner body 7B may not contact the inner surface of the outer construct 8, or may contact it (see FIG. 12 (*a*)). The outer construct 8 is inorganic fiber reinforced plastics, of which matrix is thermoplastic resin, e.g., polyether ether ketone. The adhesive filler 12 filled inside the outer body 8A is either thermoplastic resin, e.g., polyether ether ketone, or compound which chopped fiber is mixed in the thermoplastic resin.

The torsional rigidity given to the outer body 8A except the intermediate portion is regulated lower than that of the bone around the deep hollow 6 corresponding thereto, and the torsional rigidity given to the intermediate portion 18 is regulated higher than that of the bone around the deep hollow corresponding thereto (see FIG. 2, too).

The woven cloth whose fibers are arranged at an angle of approximate 45 degrees to the longitudinal axis of the stem is overlaid on the whole of surface of the outer construct 8, and the woven cloth whose fibers are arranged at an angle of other degrees is overlaid only on the local part of the surface.

The leg 8B for guiding the stem into the medullary cavity 11 in the diaphysis 5 has a cavity 14 opening at the proximal end thereof.

In the case of the inner construct 7 made of fiber reinforced plastics, the woven cloths 22 and 23 whose fibers are arranged at angles of approximate both 45 and 0/90 degrees to the longitudinal axis 21 of the stem, shown in FIG. 4, are overlaid on the whole of surface of the inner construct 7. The inner construct 7 has a shape gradually changed from the neck 7A toward the distal portion without a shoulder projecting toward the greater trochanter (see FIG. 1(*a*), too).

As shown in FIG. 11 (*a*), a portion 12*a* where the resin is not filled is formed inside the proximal end of medial side of the outer body 8A. And as shown in (*c*) of the figure, either thermoplastic resin 12A or the foam of the same is charged into the leg 8B, so that the distal portion of the outer construct 8 comes to be solid.

Fine concave grooves 32, as shown in FIG. 4 (*b*), are formed on the outer surface of the outer body 8A, especially on that of the intermediate portion 18. The outer surface of the outer body 8A is coated with hydroxyapatite 33.

A hook 10 hung on the opening edge of the deep hollow may be formed on the proximal end of medial side of the outer body 8A, as shown in FIG. 1 (*a*).

It is favorable for both of the outer construct 8 and the inner construct 7 to be divided into two halves 36, 37, 38 and 39, on the parting surface including the longitudinal axis of the individual construct, as shown in FIG. 7.

As shown in FIG. 1, the inner body 7B becomes larger in the cross section toward the distal portion except the neck 7A to have a cavity 13 opening at the distal end thereof.

As shown in FIG. 11(*b*), the leg 8B may be provided with holes 51 for passing the medicament 50 stored therein for Bone-Growth through.

As shown in FIG. 12(*c*), the inner construct may be made of cobalt alloy or titanium alloy 7Q.

Effect of Invention

According to the present invention, the outer construct may be a thin unit made of plastic molding, which is independent of the inner construct. The adjusting allowance of the rigidity of the outer construct is much wider than that of the skin of the stem without the outer construct. The thin layer of the outer construct is adaptable to the surface of a mold in the forming process, so that the outer construct can be formed easily. What has to be fitted to the shape of the deep hollow determined based on three dimensional CT graphics data is the outer construct only, not only enabling the working load during the making process thereof to be reduced in spite of a custom-made part, but also enabling the mold to lighten and miniaturize because of a thin molding. The inner construct is not required to be made precisely except the neck where the spherical head is engaged with since it does not contact the wall of the deep hollow. Accordingly, it may be a ready-made part to greatly contribute to lowering price of the stem.

Size, shape and rigidity of bone vary in response to gender, age and physique of patients, however, it is possible to design the stem in consideration of not only the pressure on the interface between the stem and the femur but also the distribution of the shearing stress based on the characteristic of the femur according to the three dimensional CT graphics thereof, resulting in that the rigidity and its distribution which are suitable for the wall strength and the shape of the deep hollow having the rigidity enough to use can be assigned to the outer construct. The outer construct comes to be adaptable to the femur, besides Fit and Fill may be improved as well as Stress-Shielding may be decreased. Moreover, it is possible to assign the design for promoting the contact-ability with the femur to the outer construct with thin structure made with ease so as to lighten the designing load of the inner construct with thick structure having few adjusting allowance of the rigidity.

According to the stem made of composite material, in which the outer body having high torsional rigidity at the intermediate portion is combined with the inner body inside thereof by adhesive filler, the rigidity given to the leg and the proximal end of the outer body is regulated lower than that at the intermediate portion of the outer body. The shearing stress concentration occurring on the interface is eliminated at the proximal end, therefore, the load acted on the wall of the deep hollow is much decreased as compared with the stem without an outer construct. The load acted on the hip joint is uniformly broadened on the proximal portion of the stem and is transmitted to the femur effectively. Unless the heavy load is locally transmitted to the femur, not only the integration of the femur with both ends of the outer construct becomes tightly but also postoperative disintegration of the cortical bone can be greatly delayed. The leg is introduced easily into the deep hollow due to the shape thereof, the low rigidity thereof reduces the load acted on the wall of the deep hollow.

The adhesive filler filled in the space between the outer body and inner body maintains the shape of the outer construct well. The elastic modulus of the filler is much lower than that of the inner body but is close to that of the outer body, therefore, the impact load transmitted to the inner body is reduced by the adhesive filler, the load to be transmitted to the outer body is dispersed, so that the wall of the deep hollow is charged only by the load with few impact, the shearing stress occurring on the interface is uniformly broadened to prevent the stem from loosening.

The majority of the load is transmitted to the proximal portion of the femur via the shortest route, so that the diffusion thereof is checked and the efficiency of transmission thereof is improved, which means the reappearance of the normal transmission process that the load transmitted from the caput is introduced into the femur. The simplification of the load distribution and the uniformity of the load on the stem make the load transmission mechanism between the femur and the stem simple, so that the promotion of Fit and Fill is applied to only the region where the load is mainly transmitted.

If the load is transmitted to the region where the load is not transmitted in a normal state by using an artificial hip joint, the load transmitted via the normal route is decreased, resulting in lowering of both the stiffness and the density of the bone at the region corresponding to the normal route due to the osteopenia. However, the reappearance of the load transmission via normal route as mentioned above promotes to grow the bone and to check the incidence of Stress-Shielding at the region. Since the stem is cement-less type, the unification with the femur depends on Bone-Growth, measures for promoting Bone-Growth is applied to at least the intermediate portion of the outer body.

In the case that the inner body is kept from contacting the inner surface of the outer construct, the inner construct is sustained by only the adhesive filler filled in the space inside the outer body. Since the adhesive filler works as a cushion between the inner construct and the outer body, it is not required to decrease the rigidity of distal end of the inner body to the limit thereof for the sake of keeping the rigidity of distal end of the outer body low, which means that the decrease of the durability of the inner construct is checked.

In the case that the distal end of the inner body contacts the outer construct, the back-up effect of the inner construct on the outer construct appears. However, in the case that the distal end of the inner body contacts the region of high rigidity of the outer body, the influence of the back-up effect remains smallest. Shortening the inner body leads the leg, which scarcely ought to be charged with the influence of contact with the inner body, to be shorter. The stem having a structure for changing the length of itself is easily also applicable to the patients of small build.

Thermoplastic resin used as matrix not only is harmless for human bodies but also realize a tough stem adaptable to a femur. The plastics reinforced with inorganic fiber such as carbon fiber, glass fiber and the like having high elasticity and high strength never fatigue like metal does. The elastic modulus of resin reinforced with the fiber is changeable depending on the number of plies and/or direction of fibers, so that the rigidity suitable for the outer construct is easily achieved by tailoring the fiber woven cloth in response to the characteristic and the rigidity distribution of the bone.

The outer body is tightly united with the adhesive filler made of thermoplastic resin for reasons of the homo-characteristic of material. The elastic modulus of the adhesive filler is much lower than that of the inner body, so that the relative deformation between the outer body and the inner body may be allowed. The adhesive filler made of the compound consisting of chopped fiber and thermoplastic resin easily realize the elastic modulas suitable for the bone-characteristic of patient by adjusting the amount of the fiber mixed in the resin.

In the case that the torsional rigidity of the outer body except the intermediate portion thereof is regulated lower than that of the bone around the deep hollow corresponding to the same of the outer body, the load passing through the region is kept low so as to check the increase in the shearing stress on the interface. On the other hand, since the torsional rigidity of the intermediate portion is regulated higher than that of the bone around the deep hollow corresponding to the intermediate portion of the outer body, the outer body never breaks before the bone corresponding to the intermediate portion of the outer body breaks, therefore, the load which is lower than the maximum strength of the bone can be always transmitted to the bone by the artificial hip joint.

Only the woven cloth whose fibers are arranged at an angle of approximate 45 degrees to the longitudinal axis of the stem is overlaid so as to cover the whole of surface of the outer construct, so that the high torsional rigidity can be given to the whole of the surface of the cylindrical outer construct. In spite of the fact that the outer construct is a rather thin structure as a whole, the reinforcement corresponding to the shearing stress in the rotational direction occurring on the interface between the femur and the outer construct before and after sitting down is effectively achieved.

The leg having a cavity opening at the proximal end thereof enables the stem to easily insert into the femur owing to the function as a guiding nose of the stem and to adapt well to the bone medullary cavity. Even if receiving an overload during the insertion of the stem, the deformable leg decreases the pressure against the bone.

In the case that the inner construct is made of fiber reinforced plastics, the woven cloths whose fibers are arranged at angles of approximate both 45 and 0/90 degrees to longitudinal axis of the stem are overlaid so as to cover the whole of surface of the inner construct. The inner body attains the structure having high rigidity withstanding the bending stress and/or torsion of the magnitude which the outer body can not endure, especially, concerning the flexural rigidity based on the tension/compression. The inner body can also be strengthened further if being additionally overlaid with uni-directional fiber from the neck to the distal portion thereof.

The inner construct having a shape gradually changed from the neck toward the distal portion without a shoulder projecting toward the greater trochanter never have the portion formed by bending the fibers at a large angle, resulting in preventing the quality of moldings from becoming unstable by the arrangement for overlaying so as not to accompany the fibers with wrinkles. Especially, the transient region from the neck to the inner body is reinforced by the uni-directional fiber providing with the characteristic of high tension/compression. The inner construction comes to be a molding with high quality so as not only to withstand the bending moment caused by the load acted on the spherical head but also to transmit the load smoothly to the outer construction.

In the case that the adhesive filler is not filled in the vicinity of the proximal portion of medial side of the outer body, the upper end of the medial side of the outer body is deformable without the disturbance due to the adhesive filler even when the bending moment caused by the vertical load acted on spherical head acts on the stem. Thereby, the load is transmitted moderately to the outer body.

In the case that the distal portion of the outer construct is solid by charging either thermoplastic resin or the foam of the same into the leg, the local deformation and wrinkles of the leg scarcely appears compared with the case of a hollow leg. The gradual deformation of the whole of leg makes it fit the medullary cavity preferably. The leg improved so as to keep the shape thereof can be also charged the residual load which the outer body could not transmit.

The fine concave grooves formed on the surface of the outer body, where the load is transmitted to the femur, can be engaged with the spongiosa grown by Bone-Growth, thereby, the unification of the stem with the femur is achieved early as well as the strength of shearing stress on the interface between them increases. Although these grooves are formed on the whole of surface of the outer construct in principle, this effect is highlighted on the intermediate portion which ought to be mainly charged by the load transmitted to the stem.

When the outer surface of the outer body is coated with hydroxyapatite, inorganic ingredients which compose enamel and dentinum promote Bone-Growth on the interface, that is, crystals of hydroxyapatite coating the stem is bonded chemically to the bone that has grown from the femur, not only enabling the stem to unite with the femur very early but also increasing the strength against shearing stress. Needless to say, coating hydroxyapatite on the intermediate portion of the outer body is most important and contributes most effectively to unite the stem with the femur.

In the case that a hook hung on the opening edge of the deep hollow is formed on the proximal end of medial side of the outer body, the touch of the hook to the opening edge of the deep hollow comes to be a stopper which tells the operator to stop the insertion of the stem, not only to avoid the over-insertion of the stem into the deep hollow but also to prevent the femur from being destroyed due to receiving the excessive hoop stress. The hook is very useful when the stem is applied to the patient of osteoporosis that the cortical bone becomes thin.

In the case that the moldings of both the outer construct and the inner construct are divided into two halves on the parting surface including the longitudinal axis of the individual construct. First, one half of the outer construct accommodating one half of the inner construct is disposed inside one finishing mold, as well as another half of the outer construct accommodating another half of the inner construct is disposed inside another finishing mold. Second, two pairs of halves are met each other by tightly closing a pair of finishing molds under the state that only the neck of the inner construct is supported in the identical molds independently of the outer construct. Finally, either thermoplastic resin or its compound is injected into the space between the outer construction and the inner construction, so that the high quality stem made of composite material can be obtained without internal defects in accordance with the principle of hydrostatic pressure.

The inner body having a cavity formed inside, whose sectional area becomes larger toward the distal portion, opening at the distal end thereof, lowers the rigidity thereof gradually toward the distal end in response to the decrease of thickness of itself. The excessively low rigidity at the distal end neither increases the rigidity which the outer body ought to have nor disturbs the distribution thereof even if the distal end of the inner body contacts the inner surface of the outer body. Forming a notch reaching the cavity around the lower portion of the neck during the re-operation for replacing an artificial hip prosthesis facilitates to deform and/or break the structural shell of the inner body, accordingly, to remove the distal portion thereof from deep hollow. The continuity of the cavity inside the leg and the cavity inside the inner body promotes to lighten the stem. Such a continuous cavity in the stem enlarges the capacity of accommodation of the medicament for Bone-Growth and medullary humor so as to keep the virtue of medicine for a certain period of time.

The holes for passing the medicament for Bone-Growth through formed on the leg allow not only the medullary humor to flow into the cavity but also the medicament mixed with the medullary humor to flow out of the cavity. The mixture appears to the interface and advances to the intermediate portion of the outer body so as to contribute to Bone-Growth and the sterilization at the region where the load is charged.

The inner construct made of cobalt alloy or titanium alloy is usable as long as it is kept from contacting the inner surface of the outer construct, for the rigidity of the inner construct and the distribution thereof have little influence on these of the outer body, which enables the inner construct to be ready-made, mass-productivity of the artificial hip joint to be promoted, resulting in facilitating of low-priced hip joint.

SYMBOLS

Figure 1:
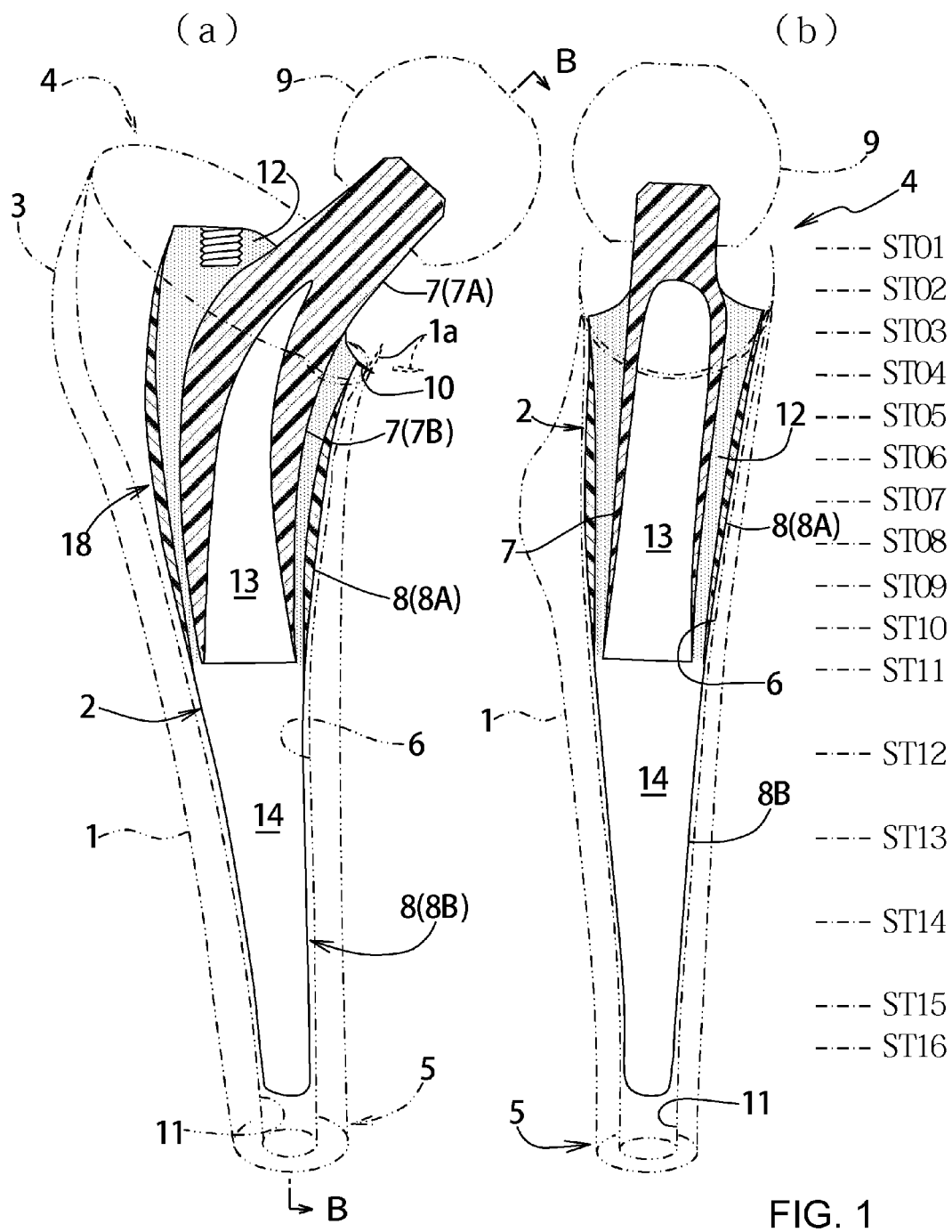
FIG. 1 is a sectional view of the artificial cement-less hip prosthesis stem according to the present invention, (a) is corresponding to the front of a body, (b) is a sectional view taking along the lines of B-B in (a).

1: femur, 2, 2A: stem, 3: greater trochanter, 4: epiphysis, 5: diaphysis, 6: deep hollow, 7: inner construct, 7A: neck, 7B, 7M and 7N: inner body, 7P: inner construct made of composite material product of a solid structure, 7Q: inner construct made of titanium alloy, 8: outer construct, 8A: outer body, 8B: leg, 8C: cap, 9: spherical head, 10: hook, 11: medullary cavity, 12 and 12A: adhesive filler, 12a: small open space, 13 and 14: cavity, 15: single-dotted chain lines (torsional rigidity of femur), 17: solid lines (torsional rigidity of stem), 18: intermediate portion, 20: thin solid line (torsional shearing stress occurred on the interface of metallic stem), 21: longitudinal axis, 22: woven cloth arranged at an angle of approximate 45 degrees, 23: woven cloth arranged at angles of 0/90 degrees to the longitudinal axis, 24: uni-directional fiber, 32: concave grooves, 33: particle of hydroxyapatite, 36~39, 38A, 38B, 39A and 39B: halves of construct, 50: medicament for Bone-Growth, 51: holes.

BEST MODE FOR CARRYING OUT THE INVENTION

Referring to the drawings of the embodiments, an artificial cement-less hip prosthesis stem according to the present invention is disclosed as follows; FIG. 1(a) is a sectional view in which a stem 2 is implanted into a femur 1, and (b) is a sectional view taken along lines B-B in (a), wherein the stem is implanted in a deep hollow 6 extending from the epiphysis 4 to the diaphysis 5 of the femur by excising some spongiosa and a part of medulla so as not to pass through a greater trochanter 3, gradually united with the femur 1 by Bone-Growth, enabling the artificial cement-less hip prosthesis stem to eliminate the interfacial separation.

The stem 2 mainly consists of an inner construct 7 and an outer construct 8, the former is provided with a neck 7A and an inner body 7B, the latter is provided with an outer body 8A and a leg 8B. The neck 7A is engaged with a spherical head 9 which works as a joint in cooperation with a socket, not shown, fixed to a pelvis, so as to transmit a load acted on a hip joint to the stem 2. The inner body 7B is continuous with the neck 7A reacting with the load transmitted from the neck to the outer construct 8. The inner construct is located at longitudinal axis of the stem 2, having a shape gradually changed from the neck toward the distal portion without a shoulder projecting toward a greater trochanter.

The above-mentioned outer body 8A has an after-mentioned hook 10 hung on the opening edge of the deep hollow on the proximal end of the medial side, being bell mouth-shaped toward the epiphysis so as to surround the inner body 7B. The leg 8B is originally united with the distal end of the outer body, being like a long cone extending toward the medullary cavity 11. In this example, the outer body 8A is formed with the leg 8B originally as a uni-molding.

The adhesive filler 12 is filled in the space between the inner body 7B and the outer body 8A for combining with each other, the outer surface of the outer body contacts most of the wall of the deep hollow 6 so as to transmit the load acted on the inner body 7B to the femur 1. The outer construct 8 is made of fiber reinforced plastics, but the inner construct 7 is not necessarily made of it. In this example, the inner construct 7 is also made of fiber reinforced plastics and the distal end of the inner body 7B does not directly contact the inner surface of the outer construct 8.

The stem 2 is described more in detail as follows; the torsional rigidity given to the proximal end and distal end of the outer body 8A and the whole of the leg 8B is regulated lower than the torsional rigidity of the intermediate portion of the outer body 8A, resulting in transmitting the load distributed collectively on the intermediate portion to the proximal portion of the femur as uniformly as possible. The inner body 7B becomes larger in the cross section toward the distal portion except the neck 7A and has a cavity 13 opening at the distal end inside thereof. The leg 8B, mentioned above, guides the stem into the medullary cavity 11 in the diaphysis 5, inside the leg having a cavity 14 opening at the proximal end thereof.

The object of the present invention is to intend to make the route for transmitting the load under the use of an artificial hip joint close to that under a normal state as much as possible, so that the load acted on the hip joint may not be concentrated on both the distal end of the stem 2 and the proximal end of medial side thereof. Therefore, the varied distribution of the torsional rigidity is assigned to the outer body 8A as follows; which makes possible because the outer construct 8 is made of fiber reinforced plastic and is a thin uni-structure.

Figure 2:
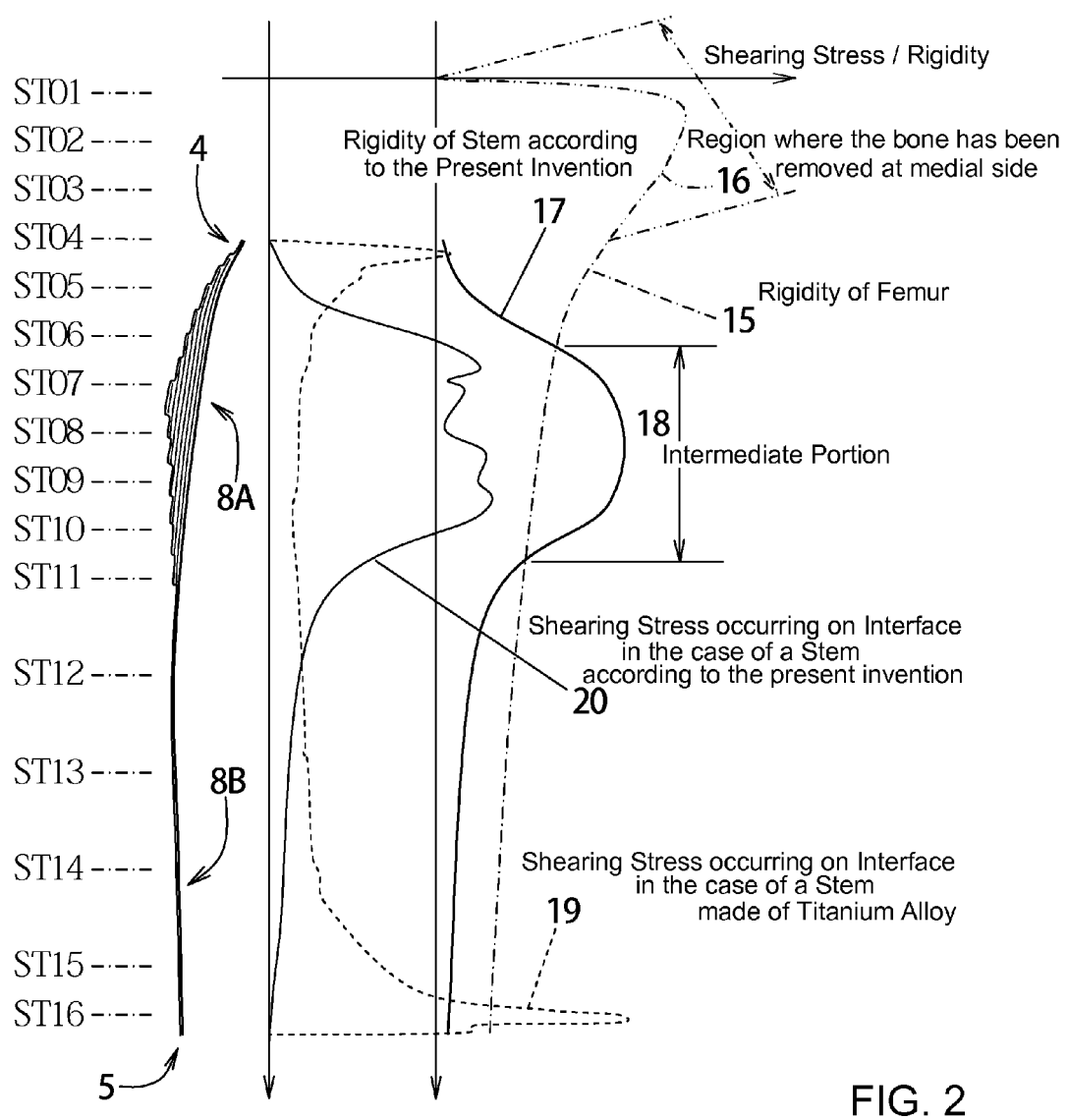
FIG. 2 is a graph of torsional shearing stress acted on the interface of medial side of the stem and the rigidity distributions of the femur and the outer construct.

FIG. 2 is a graph where the cross section of the medial side of the outer construct and the torsional rigidity on the wall of the deep hollow corresponding thereto are illustrated in association with the torsional shearing stress acted on the interface between the outer construct and the wall of the deep hollow. The indications at the left side of the figure show the same stations in the longitudinal direction that are appeared at the right side of FIG. 1. The view on the right side of the indications is a cross sectional view of the medial side of the outer body 8A and the leg 8B, being identically to FIG. 3 (c) mentioned after. The single-dotted chain line 15 in FIG. 2 indicates the torsional rigidity of the femur (equal to the wall of the deep hollow). Since the cross section at epiphysis of the femur is much larger than that at the diaphysis as indicated in FIG. 1, the torsional rigidity naturally decreases toward the medullary cavity. Usually, either cortical bone does not originally have the upper part over ST04 at the medial side or the part of reference number 1a in FIG. 1 (a) is removed during operation. The double-dotted chain line 16 which continues on the single-dotted chain line 15 mentioned above indicates the rigidity estimated on the assumption that a closed space is formed by the cortical bone of lateral side and the supposed cortical bone of medial side.

The solid line 17 in FIG. 2 indicates the distribution of the torsional rigidity given to the stem. In this case, the torsional rigidity given to the outer body 8A except the intermediate portion 18 is regulated lower than the torsional rigidity (see line 15) of the bone around the deep hollow corresponding to the outer body except the intermediate portion, the torsional rigidity given to the intermediate portion 18 is regulated higher than the rigidity of the bone around the deep hollow corresponding to the intermediate portion, thereby, the route for transmitting the load is made to be close to that in a normal state as much as possible. The rigidity of the outer body 8A is regulated to change gradually higher at the region from the proximal portion toward the intermediate portion and gradually lower at the region from the intermediate portion toward the distal portion of the outer body, so as to smoothly change the shearing stress occurring on the interface. Since the load acted on the bone neither increase nor decrease suddenly, the outer body 8A seldom comes loose on the wall of the deep hollow. The intermediate portion 18 corresponds to the part of 5 to 40% from the proximal end in the scale shown at right of FIG. 3 (c) mentioned after.

As mentioned above, when the torsional rigidity given to the outer body 8A except the intermediate portion 18 is regulated lower than the torsional rigidity of the bone around the deep hollow corresponding thereto, the load transmitted on the outer body except the intermediate portion does not become high, so that the increase in the shearing stress on the interface is checked. Meanwhile, since the torsional rigidity given to the intermediate portion 18 is regulated higher than the torsional rigidity of the bone around the deep hollow corresponding to the intermediate portion, the bone and the outer body react on each other at the intermediate portion within the limits that the bone does not break down. The outer body 8A is never destroyed before the bone corresponding to the intermediate portion of the outer body is destroyed, so that the load is always transmitted to the bone, and vice versa, within the maximum allowable strength of the bone.

Figure 15:
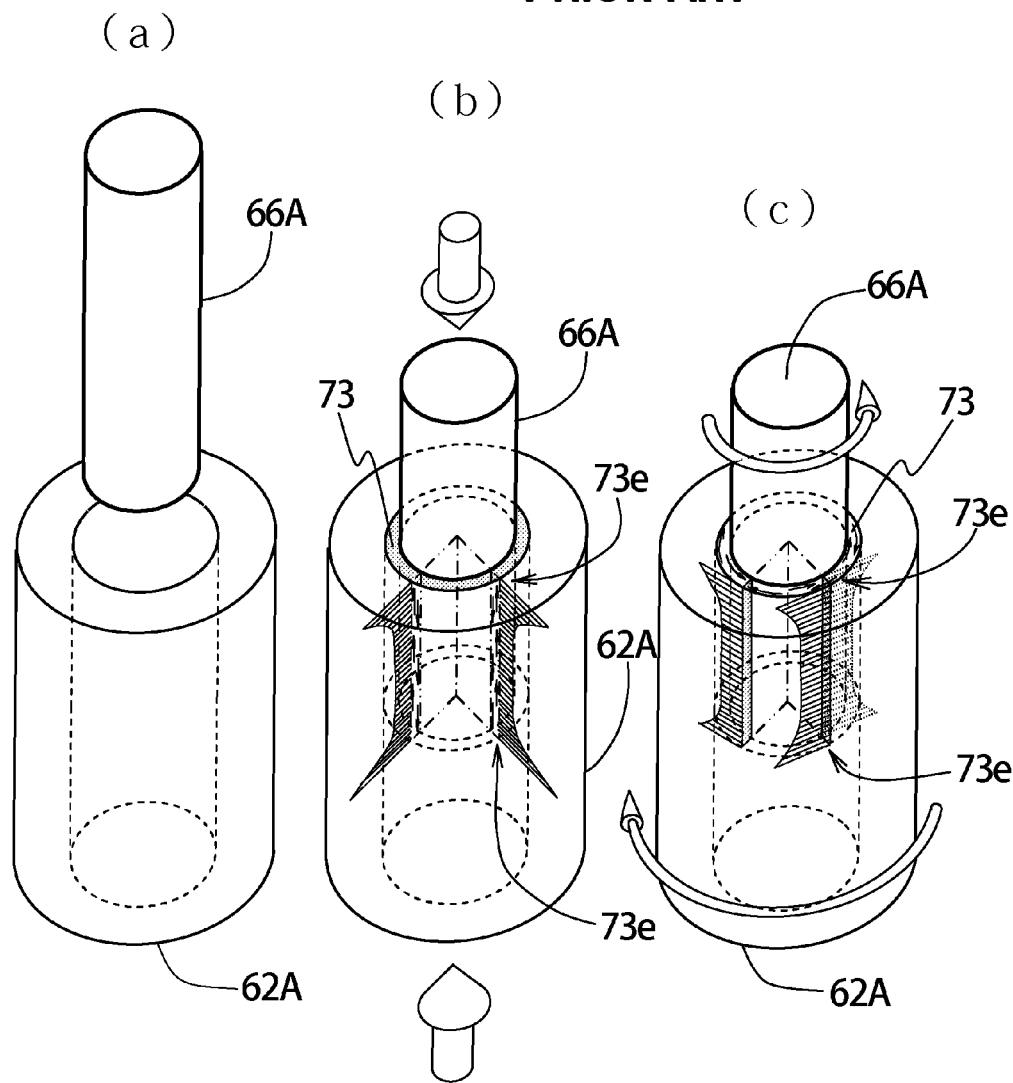
FIG. 15 is explanatory diagrams showing the shearing stress occurring on the adhesive jointing layer under the state that two cylinders are overlapped with each other.

The broken line 19 in FIG. 2 indicates the distribution of torsional shearing stress occurring on the interface in the case of a metallic stem. As described in FIG. 15, the stress concentrates at both the end of the epiphysis 4 and the end of the diaphysis 5. However, according to the stem of the present invention, as shown by the thin solid line 20, the stress is distributed collectively on the intermediate portion 18, moreover, the range of variation of the stress comes to be narrow on the whole, which is obvious that the distribution of load is similar to that under the normal state. The torsional rigidity given to the leg 8B may be regulated constant, but may be also regulated lower toward the distal portion as shown by the lower half of a solid line 17, then, the shearing stress occurring on the interface becomes gradually lower similarly to the line, resulting in promoting the contact-ability with the wall of the deep hollow.

The inventors of the present invention have experimented and analyzed a lot to have obtained the new knowledge that the magnitude and the distribution of torsional shearing stress occurring in the rotational direction of the interface in relation to the motion before and after sitting down are influenced much more greatly by the rigidity of the outer construct than that of the inner construct, therefore, it is important that the varied rigidity is given to the outer construct and, particularly, that the torsional rigidity is regulated much higher on the region for transmitting load, consequently, the torsional stress is not concentrated at the proximal end and the distal end of the outer construct. Furthermore, the inventers have also obtained another knowledge that the tension/compression shearing stress occurring in the longitudinal direction of the interface in relation to the motion during uprightly standing and walking depends much more greatly on the rigidity of the inner construct than that of the outer construct, and that the rigidity of the region for transmitting load of the outer construct may be regulated constant and as low as the tension/compression rigidity of the cortical bone although the rigidity in the longitudinal direction of the inner construct has to be kept high.

The point described above is as follows: it is important that the tension/compression caused by the bending moment acted on the stem is charged mainly on the inner construct and the torsion acted on the hip joint is charged mainly on the outer construct in order to transmit them to the femur. The philosophy that two counter concepts of design are applied to a unit of stem often obliges to accept the unsatisfactory function and performance of the stem. However, the stem according to the present invention consists of plural parts in which the specific design concept is applied individually, so that each part facilitates to have an ideal function and performance, for the designing load of individual parts is lightened by keeping us from compromise on designing.

Figure 3:
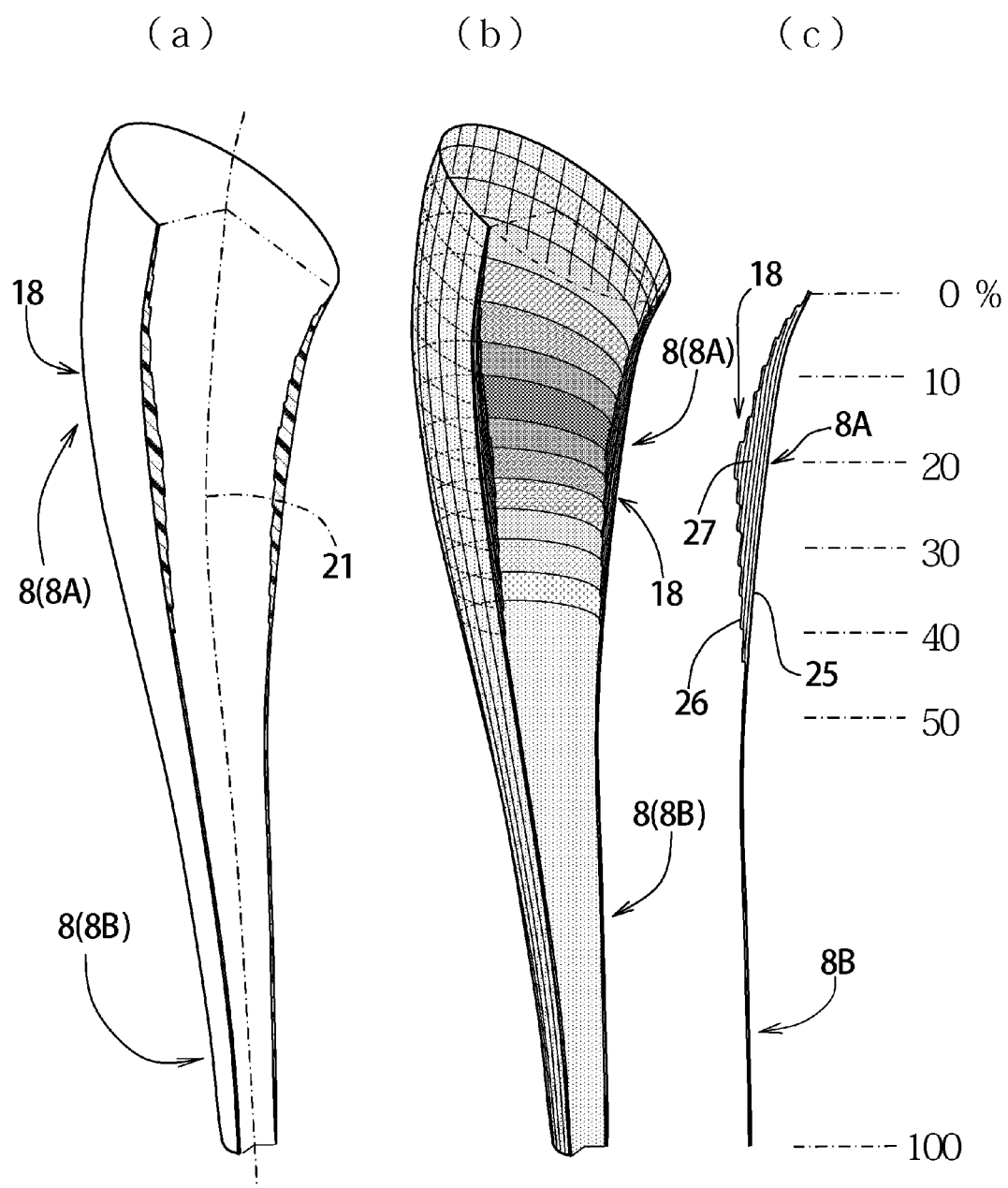
FIG. 3 shows the outer construct, (a) is a perspective exploded view, (b) is a perspective exploded view showing the overlaying structure without the most inner layer and (c) is a cross sectional view exaggeratedly showing the state of the layer of the medial side of the outer construct.

In order to increase the torsional rigidity of the stem the direction of the fibers of composite material is made not to agree with the direction of torsion acted on the stem, e.g., at angles of approximate ±45 degrees to the direction of torsion; therefore the woven cloth whose fibers are arranged at an angle of approximate 45 degrees to the longitudinal axis 21 (see FIG. 3(a)) of the stem is overlaid on the whole of surface of the outer construct. It is adequate for the outer construct to be able to withstand the shearing stress only acted at an angle of 45 degrees to the longitudinal direction of the stem. Because the adjustment of the rigidity in response to the load in the axial direction scarcely contributes to the reduction of the shearing stress caused by the tension/compression acted on the interface. The varied torsional rigidity can be realized easily by changing the number of layers of fiber woven cloth, as shown in FIG. 3 (b).

In order to reinforce the stem in response to the tension/compression acted thereon during uprightly standing and walking, the woven cloths whose fibers are arranged at angles of approximate 0/90 degrees and uni-directional fibers, not shown, are overlaid additionally. In the medial portion where the flexural rigidity is desired to increase intensively, the reinforced fiber is arranged at right angle to the direction of axis of the stem. In the case that such cloths and fibers are added to the outer body 8A, they are applied to only the intermediate portion 18 corresponding to the proximal portion of the stem, under the condition that the rigidity of the intermediate portion never comes to be larger than the tension/compression rigidity of wall of the deep hollow, i.e., so as to balance with the hoop stress acted on the interface.

As shown in FIG. 4(a), the inner construct 7 is overlaid with the woven cloth 22 whose fibers are arranged at a angle of approximate 45 degrees to the longitudinal axis 21 of the stem and with the woven cloth 23 whose fibers are arranged at angles of approximate 0/90 degrees to the longitudinal axis of the stem on the whole of surface of the inner construct, and the uni-directional fibers 24 is overlaid on the range from the proximal portion to the distal portion if necessary. The latter two are mainly used by reason that they are charged by the tension/compression, the former, the woven cloth whose fibers are arranged at a angle of approximate 45 degrees, is overlaid on the outside surface or the neighborhood so as to realize the torsional rigidity with a few layers as possible.

Owing to such a layer structure, the inner body has high rigidity for the tension/compression of the magnitude which the outer body can not endure and can withstand the bending moment caused by the inclination of the neck 7A to the inner body 7B.

The composite material applied to the outer construct 8 and inner construct 7 is fiber reinforced plastics, of which matrix is thermoplastic resin, e.g., harmless polyether ether ketone or polyrther imido, and of which reinforcing material is inorganic fiber, e.g., carbon fiber or glass fiber. The thermoplastic resin as matrix is harmless for human bodies because it neither is hygroscopic nor lixiviate, furthermore, it is so tough that it can make the outer construct adopt to the femur without damage even when the outer construct is forced to be deformed. The carbon fiber and the glass fiber as the reinforcement have high elasticity and high strength, e.g., the maximum elastic modulus of the carbon fiber attains to 630 GPa, besides never fatigue like metal does. Although the fiber for reinforcing is highly elasticity, the rigidity thereof can be adjustable by changing the arrangement and amount of the fiber woven cloth, thus the design for making the stem comes to be remarkably flexible.

The inner construct does not have a shoulder with sharp curves so that the fiber woven cloth is overlaid to be the smooth lamination without wrinkles, which enables the quality of moldings to be stable. Especially, the transitional region from the neck to the inner body can be reinforced by unidirectional fibers having the characteristic of high tension/compression, so that the moldings without internal defects can be made at high strength and high quality, resulting in transmitting the load from the spherical head to the femur smoothly and in enduring the bending moment acted on itself.

The stem made of fiber-reinforced plastics is fabricated by combining the outer construct and the inner construct made as described above. Changing the number of plies of fiber woven cloth and the direction of fibers enables an anisotropic stem to have varied rigidity. Tailoring the fiber woven cloth in response to the characteristic and the rigidity distribution of the bone can provide a stem which is highly conformable to orthotropic bone in comparison with an isotropic metallic stem or a metallic stem covered with fiber reinforced plastic.

The inventors have also found that the compression shearing stress occurring on the interface has a tendency to concentrate further on the proximal portion of the stem in proportion to the thickness of the adhesive filler. Therefore, as shown in FIG. 1, the inner body 7B is surrounded by the adhesive filler 12, thereby, not only the compressive load is distributed collectively on the intermediate position 18 of the outer body 8A but also the concentration of shearing stress caused by the compression as shown FIG. 15 (b) is eliminated. It is worthy of notice that the stem 2 is provided with the space for accommodating the adhesive filler 12 originally because it consists of the outer body 8A which is bell mouth-shaped and the inner body 7B which is slim without a shoulder. The space between the outer body and the inner body becomes smaller from the proximal portion toward the distal portion as shown in FIG. 1, preventing the adhesive filler 12 from advancing into the leg 8B at the distal end of the inner body 7B.

The adhesive filler filled mentioned above is either thermoplastic resin or the compound in which the chopped fiber is mixed in the thermoplastic resin as described above. The properties of the compound is similar to those of the thermoplastic resin already explained, therefore, the elastic modulus of the adhesive filler is much lower than that of the inner body 7B, and is very close to that of the outer body 8A. The adhesive filler 12 is tightly united with the outer body because of the homo-characteristic of the material. Since the elastic modulus of the adhesive filler is much lower than that of the inner body 7B, the relative deformation of the adhesive filler to the inner body is allowable, resulting not only in the absorption of a part of torsion of the inner body but also in the reduction in shearing stress occurring on the interface.

It is possible to increase more in the elastic modulus of the thermoplastic resin compound containing chopped fiber than that of the resin by itself. The possibility of increase in the elastic modulus leads to widen the allowance for adjusting the elastic modulus so as to fit easily to the properties of the bone of patients. The chopped fiber makes a bridge in the compound near the distal end of the inner body 7B to prevent the resin from advancing further. Moreover, it is fatigueless like the resin by itself, of course, the durability thereof is superior to that of metallic stem.

FIG. 3 is a schematic view with a partial section of the outer construct 8 formed as a uni-molding consists of the outer body 8A and the leg 8B. Although the structure of the outer construct is thin, the portion overlaid with a lot of plies is drawn thickly as (a) of the figure in order to see clearly that it is made of fiber reinforced plastic. (b) is a perspective exploded view showing the state where the outer construct is overlaid inwardly, wherein the most inner layer mentioned after is omitted. (c) is a cross sectional view exaggeratedly showing the state of the layer of the medial side of (b). It shows clearly that the middle layer 27 consisting of several layers is covered with the most outer layer 25 and the most inner layer 26 of the outer construct 8.

Figure 5:
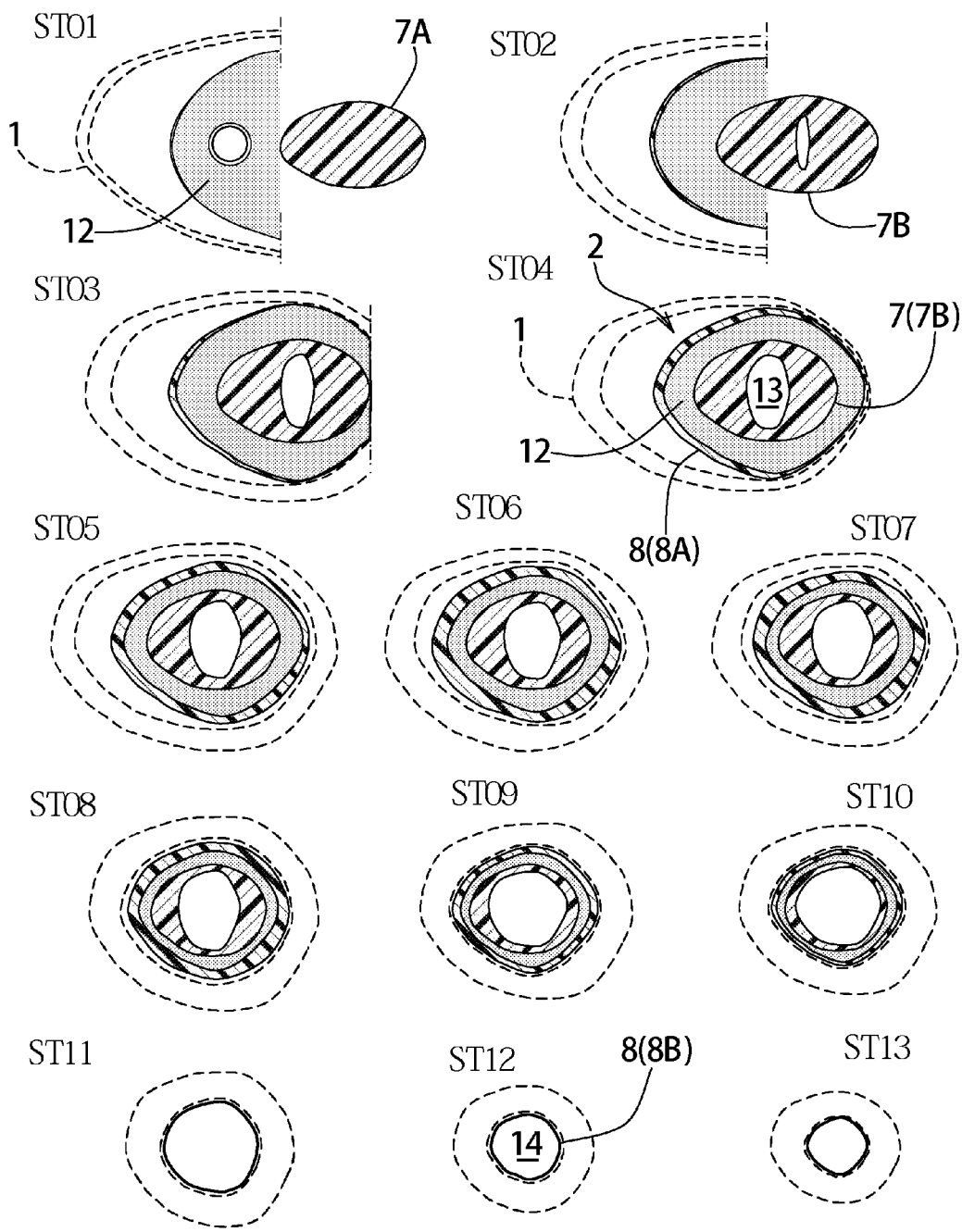
FIG. 5 is sectional views on each station in FIG. 1

Each layer is formed by overlaying one or several piles made of fiber woven cloth and resin spun cloth. In every part of the outer construct, the piles are overlaid so that the fibers thereof are arranged at an angle of approximate 45 degrees in a mold. The woven cloth whose fiber is arranged at angles of 0/90 degrees may be overlaid if necessary. The overlaid plies in the mold are heated by means of an autoclave, the melted resin turns into matrix to be a layer article containing the fibers. FIG. 5 is sectional views of the bone and the stem at some stations, wherein the thickness of cortical bone, thickness of the outer construct 8, and layer thickness of the adhesive filler 12 are changed as mentioned before.

As shown in FIG. 1, the composite material stem 2 consists of the outer body 8A whose torsional rigidity is increased on the intermediate portion 18 and the inner body 7B disposed inside the outer body and the adhesive filler 12 which bonds the outer body and the inner body. The stem broadens uniformly the load acted on the hip joint on the proximal portion of the stem to transmit it to the femur, resulting in eliminating the shearing stress concentration on the both ends of the interface caused by the torsion or the tension/compression. The stem of the present invention, unlike the conventional stem without the outer construct (see FIG. 16), hardly makes the heavy load act on the femur locally, so that the patients are free from the anxiety about the postoperative disintegration of the cortical bone.

The rigidity given to the whole of leg 8B, the proximal end and the distal end of the outer body 8A is regulated lower than the rigidity given to the intermediate portion 18 of the outer body 8A, as mentioned before, lowering the rigidity thereof much more makes the shearing stress occurring at the both ends of the outer construct very low. Not only the femur is united with the both ends of the outer construct more tightly but also the load can be distributed collectively on the intermediate portion. The outer shape of the leg 8B makes the stem insert smoothly into the deep hollow, the low rigidity thereof reducing the load acted on the wall surface of the deep hollow.

The leg 8B works as a guiding nose while it is inserted into the medullary cavity 11, the cavity 14 opening at the proximal end makes the leg adapt well to the medullary cavity. Since the deformation thereof is permitted even if the excessive load is charged on the leg during the insertion, the pressure acted on a bone decreases. The reinforced fiber is arranged at an angle of approximate 45 degrees to the longitudinal axis of the stem to form the outer construct, so that the guiding nose can display the higher flexibility in the vertical and horizontal directions of the leg.

In the case that the inner body is kept from contacting the inner surface of the outer construct, the inner construct 7 is sustained by only the adhesive filler 12 filled in the space inside the outer body 8A. The adhesive filler works as a cushion in the space between the inner construct and the outer body. Accordingly, it is not required to decrease the rigidity of distal end of the inner body to the limit thereof for the sake of keeping the rigidity of distal end of the outer body 8A as low as possible. This means that the decrease in the durability of the inner construct 7 can be checked.

The adhesive filler filled in the space between the outer body and inner body maintains the shape of the outer construct well. The elastic modulus of the filler is much lower than that of the inner body but is close to that of the outer body, therefore, the impact load transmitted to the inner body is reduced by the adhesive filler, the load to be transmitted to the outer body is dispersed, so that the wall of the deep hollow is charged only by the load with few impact, the shearing stress occurring on the interface is uniformly broadened to prevent the stem from loosening, as a result, the stem comes to be usable for a long period.

The hook 10 provided on the proximal end of the outer body 8A comes to be stopper for telling an operator to stop the insertion of the stem on condition that it touches an opening edge formed beforehand by cutting off the upper portion 1a of the cortical bone as shown in FIG. 1 (a). Avoiding the over-insertion of the stem into the deep hollow prevents the femur from being destroyed by the excessive hoop stress and a patient from suffering from dolor caused by the break of the femur. More than two hooks are also available, and they are required to be flanges or fins having shape and size which do not reinforce the upper portion of the outer body 8A being in low rigidity in spite of the number of hooks. The hooks are very useful when the stem is applied to the patient of osteoporosis that the cortical bone has become thin.

The outer construct of the aforementioned stem is a unit molding forming a thin structure independently of the inner construction. The adjusting allowance of the tension/compression rigidity and torsional rigidity of the outer construct is much wider than that of the skin of the stem (see FIG. 16) without the outer construct, resulting in facilitating to assign the varied distribution of the torsional rigidity to the outer body. The potential for making a low rigidity portion on the outer body supports to give a high rigidity to the intermediate portion of the bell mouth-shaped shell and to give a varied rigidity and/or an extremely low rigidity to the portion except the intermediate portion of the outer body. The stem made of composite material is reliable on durability because it never fatigue unlike metallic stem does.

The majority of the load is transmitted to the proximal portion of the femur via the shortest route, so that the diffusion of the load is checked and the efficiency of transmission thereof is improved. This means the reappearance of the normal transmission process that the load transmitted from the caput is introduced into the proximal portion of femur. The simplification of the load distribution and the uniformity of the load on the stem make the load transmission mechanism between the femur and the stem simple, so that the promotion of Fit and Fill is required on only the region where the load is mainly transmitted.

If the load is transmitted to the region where the load is not transmitted in a normal state by using an artificial hip prosthesis, the load transmitted via the normal route decreases. Once the osteopenia caused by Stress-Shielding appears, both the stiffness and the density of the bone are lowered on the normal route. However, the reappearance of the load transmission via normal route promotes the growth of bone to check the incidence of Stress-Shielding at the region.

Figure 10:
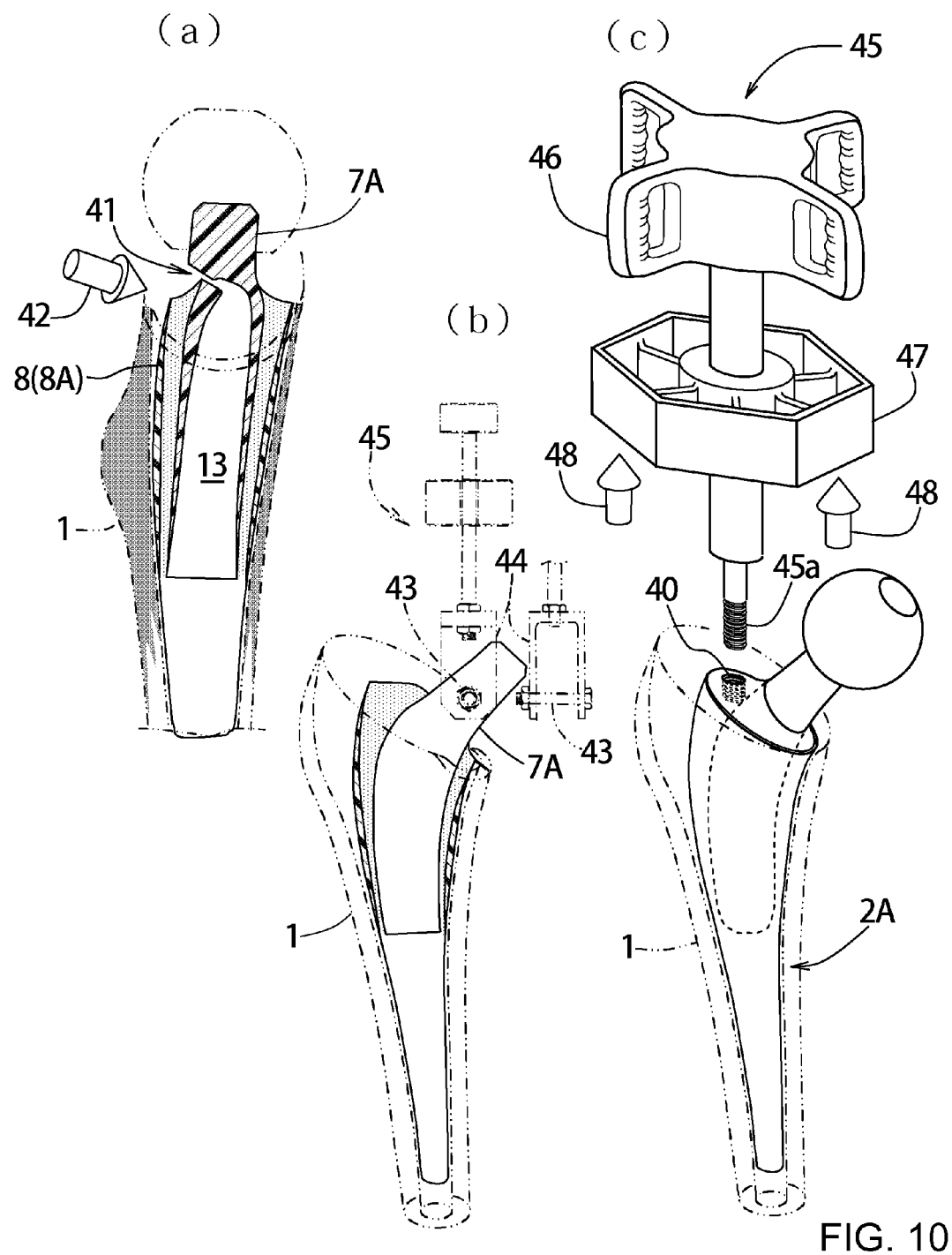
FIG. 10 is an explanatory diagram where the stem according to the present invention is removed from the femur.
Figure 11:
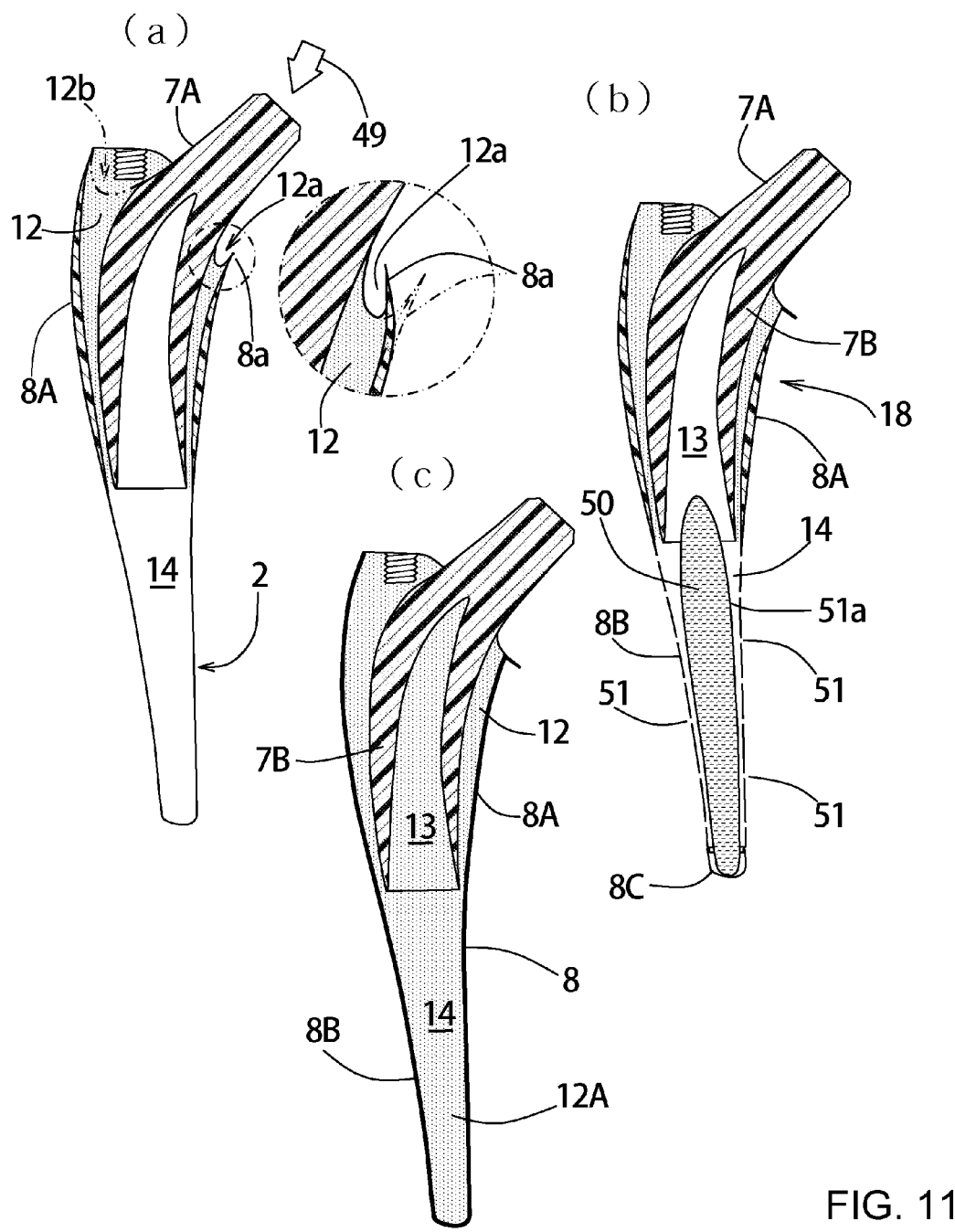
FIG. 11 shows; (a) is a sectional view of the stem provided with the small open space where resin is not filled, accompanied with an enlarged sectional view around the small open space, (b) is a sectional view of the stem storing a capsule containing medicament for Bone-Growth in the leg and (c) is a sectional view of the stem whose cavity is filled with the foaming resin.

The inner body 7B has a cavity 13 formed inside. Since the cavity opening at the distal end thereof has the sectional area which becomes larger toward the distal portion, it lowers the rigidity thereof gradually toward the distal end in response to the decrease in thickness of itself. The excessively low rigidity of the distal end neither increases the rigidity which the outer body ought to have nor changes the distribution thereof even if the distal end of the inner body contacts the inner surface of the outer body 8A. The continuity of the cavity 13 inside the inner body and the cavity 14 inside the leg promotes to lighten the stem. As shown in FIG. 10 (a) explained later, forming a notch 41 reaching the cavity 13 around the lower portion of the neck 7A during the re-operation for replacing an artificial hip prosthesis facilitates to remove the portion from the notch to the distal portion of the inner body from the femur 1. The continuous cavities mentioned above in the stem enlarge the capacity of accommodation of the medicament 50 for Bone-Growth and medullary humor as shown in FIG. 11 (b), so as to keep the virtue of medicine for a certain period of time.

Size, shape and rigidity of bone vary in response to gender, age and physique of patients. However, it is possible to design the stem in consideration of not only the pressure on the interface between the stem and the femur but also the distribution of the shearing stress based on the characteristic according to the data of three dimensional CT graphics of the femur. As a result, the rigidity and its distribution which are suitable for the wall strength and the shape of the deep hollow having the rigidity enough to use can be assigned to the outer construct. The outer construct comes to be adaptable to the femur, besides Fit and Fill may be improved as well as Stress-Shielding may be decreased. Moreover, it is possible to apply the design for promoting the contact-ability with the femur to the outer construct having thin structure made with ease so as to lighten the designing load of the inner construct with thick structure having few adjusting allowance of the rigidity.

The thin layer of the outer construct is adaptable to the surface of a mold in the forming process, so that the outer construct can be formed easily without the troublesome complicated pressure control in the mold. What has to be fitted to the shape of the deep hollow determined in accordance with the three dimensional CT graphics data is the outer construct alone. The accuracy on the forming by means of molds does not need to be exact because of the existence of some fine concave grooves on the surface of the outer body and of the forming of an undersize hollow excised by means of medical rasp. In spite of the fact that the outer construct is a custom-made part, the construct with low rigidity promotes to lighten and to miniaturize the mold. The inner construct is not required to be made precisely except the neck engaged with the spherical head since it does not contact the wall of the deep hollow, accordingly, it may be a ready-made part to greatly contribute to lowering price of the stem.

Figure 6:
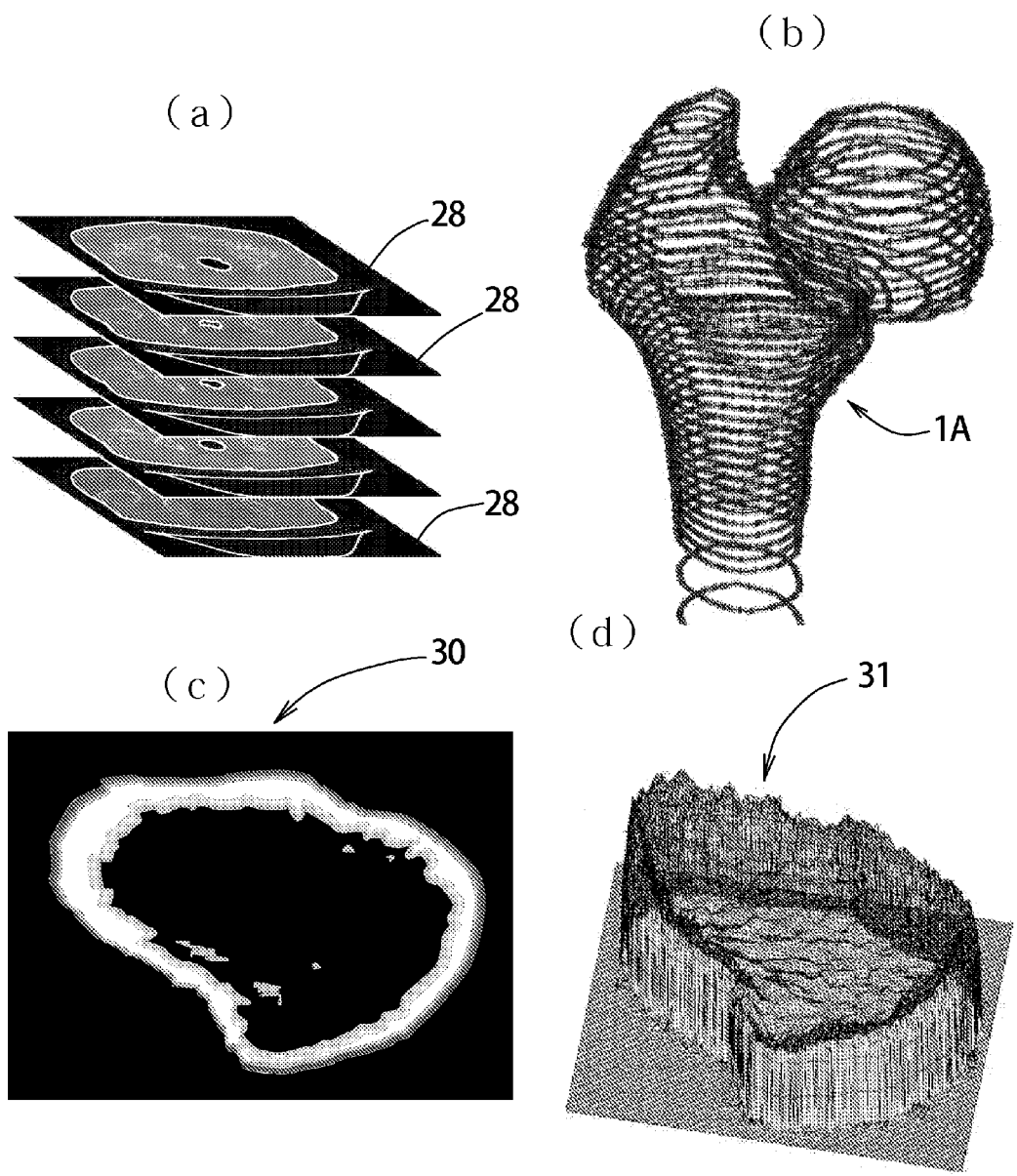
FIG. 6 shows processes of the quality examination of the femur, (a) is a number of CT graphics taken before the operation, (b) is a reproductive view of the femur obtained by the three-dimensional process of the graphics, (c) is a graphic showing the density of bone on one cross section, (d) is a stereoscopic figure of a distribution of the density on one cross section.

The processes for determining the shape and size of the deep hollow and the shape, size and rigidity of the outer construct according to the three dimensional CT graphics data are described as follows: As shown in FIG. 6 (*a*), a number of tomograms 28 of a patient's femur are taken, overlapping the tomogram processed by a computer to present the profile of a femur 1A as shown in (*b*) of the figure. The density of cortical bone and spongiosa obtained from the image 30 shown in (*c*) of the figure at individual tomogram gives us the elastic modulus and the rigidity at every cross section of the femur, which is easily supported by use of the well-known data of the rigidity in relation to the density of bone. (*d*) of the figure shows a stereoscopic figure of a distribution 31 of the rigidity on one cross section. The contour of the deep hollow is determined according to the degree of bone density on each cross section, piling the individual contour 3-dimentionally provides us the shape to be excised by a medical rasp. All of data of rigidity of bone around the deep hollow tell us beforehand the strength of the femur after the prosthesis.

Figure 4:
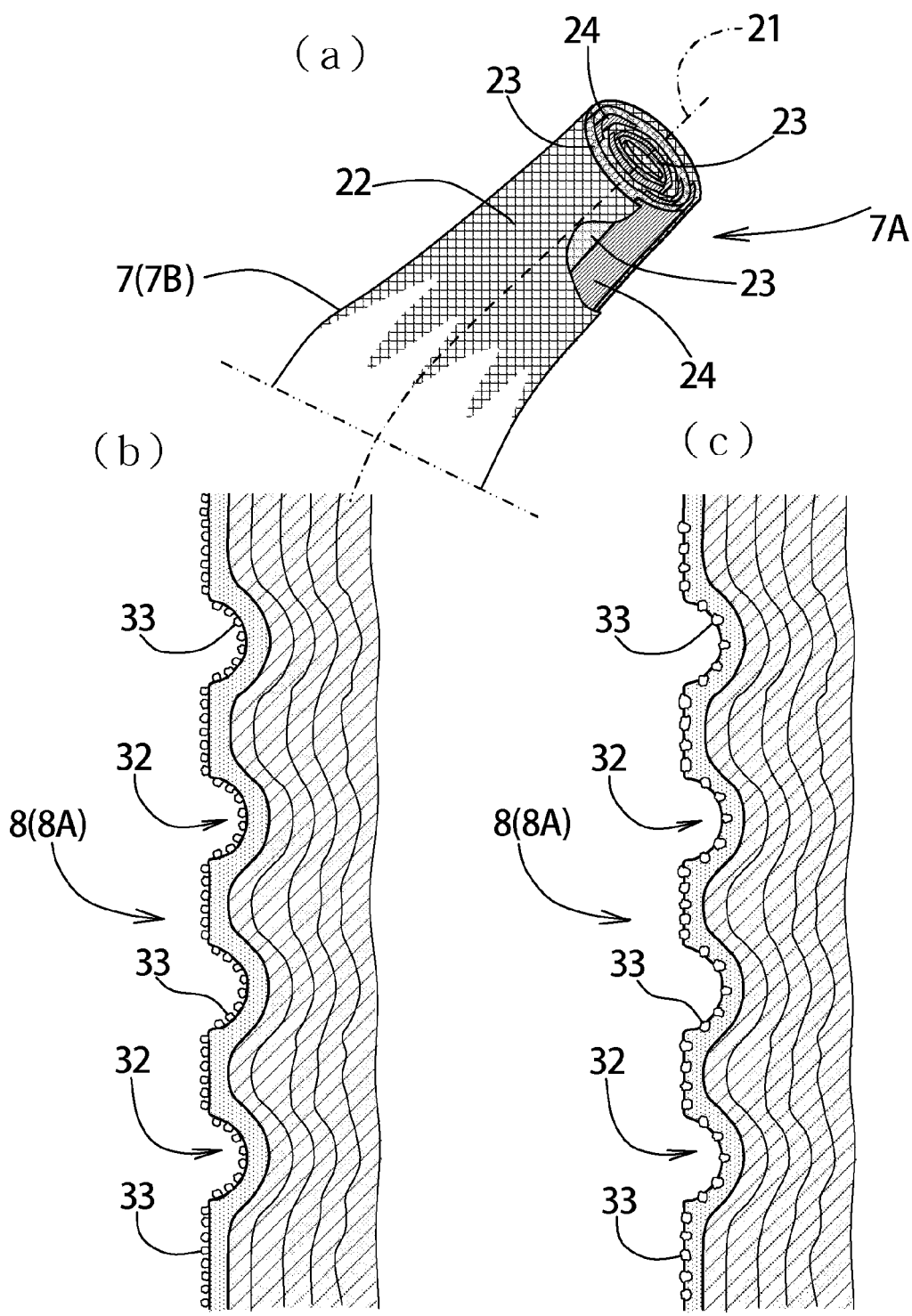
FIG. 4 (a) is a perspective view showing the overlaid structure of the inner construct, (b) and (c) are enlarged schematic view of the outer constructs being treated for Bone-Growth.

It is preferable to form many fine concave grooves 32 shown in (*b*) and (*c*) of FIG. 4. They extend in the vertical and/or horizontal directions on at least the outer surface of the outer body 8A being a part of the outer construct which contacts the wall of the deep hollow so as to accelerate to unite the stem with the femur by Bone-Growth. The advance of the spongiosa having just grown into the grooves promotes to unite the stem with the femur, so that the shearing strength displayed on the interface between them increases gradually. These grooves 32 may be formed on the whole of surface of the outer construct. Especially, it is most important to form the grooves mainly on the intermediate portion 18 (see FIG. 1) of the outer body 8A in consideration of the fact that Bone-Growth becomes active on the region charged with the stimulation due to the load transmitted.

Although the grooves 32 may also be formed by the surface treatment after the outer construct 8 has been molded, it is more preferable to form them while molding the stem, for all the surfaces of grooves can be coated with resin matrix so as not to make the fiber appear even if the grooves are, e.g., 0.5 mm in width and 0.25 mm in depth.

In addition to the forming of the grooves mentioned above, it is much more preferable to coat the particles 33 of hydroxyapatite on the surface of the stem as shown in FIG. 4 (*b*), or to bury them under the surface as shown in (*c*). In the case of burying them the resin sheet impregnating with crystals of hydroxyapatite is disposed on the surface of the bottom of a mold before molding the outer construct. Hydroxyapatite is inorganic ingredients which compose enamel and dentinum to promote Bone-Growth on the interface, that is, crystals of hydroxyapatite distributed on the stem is bonded chemically to the bone having grown from the femur, not only enabling the stem to unite with the femur very early but also increasing the strength against shearing stress.

Such a processing on the intermediate portion 18 of the outer body 8A is most effective to unite the stem with the femur. The elimination of Micro-Movement and Interfacial Separation not only makes the stem not generate worn powder causing carcinogenesis but also prevents patients from suffering from sharp pain caused by loosening the stem. It is possible to coat both the inside of the grooves 32 and the neighborhood thereof with hydroxyapatite. Even if the grooves are not formed on the stem, the function of hydroxyapatite for promoting Bone-Growth never decreases. Accordingly, the use of both grooves and hydroxyapatite makes the hip joint reappear very early.

Figure 7:
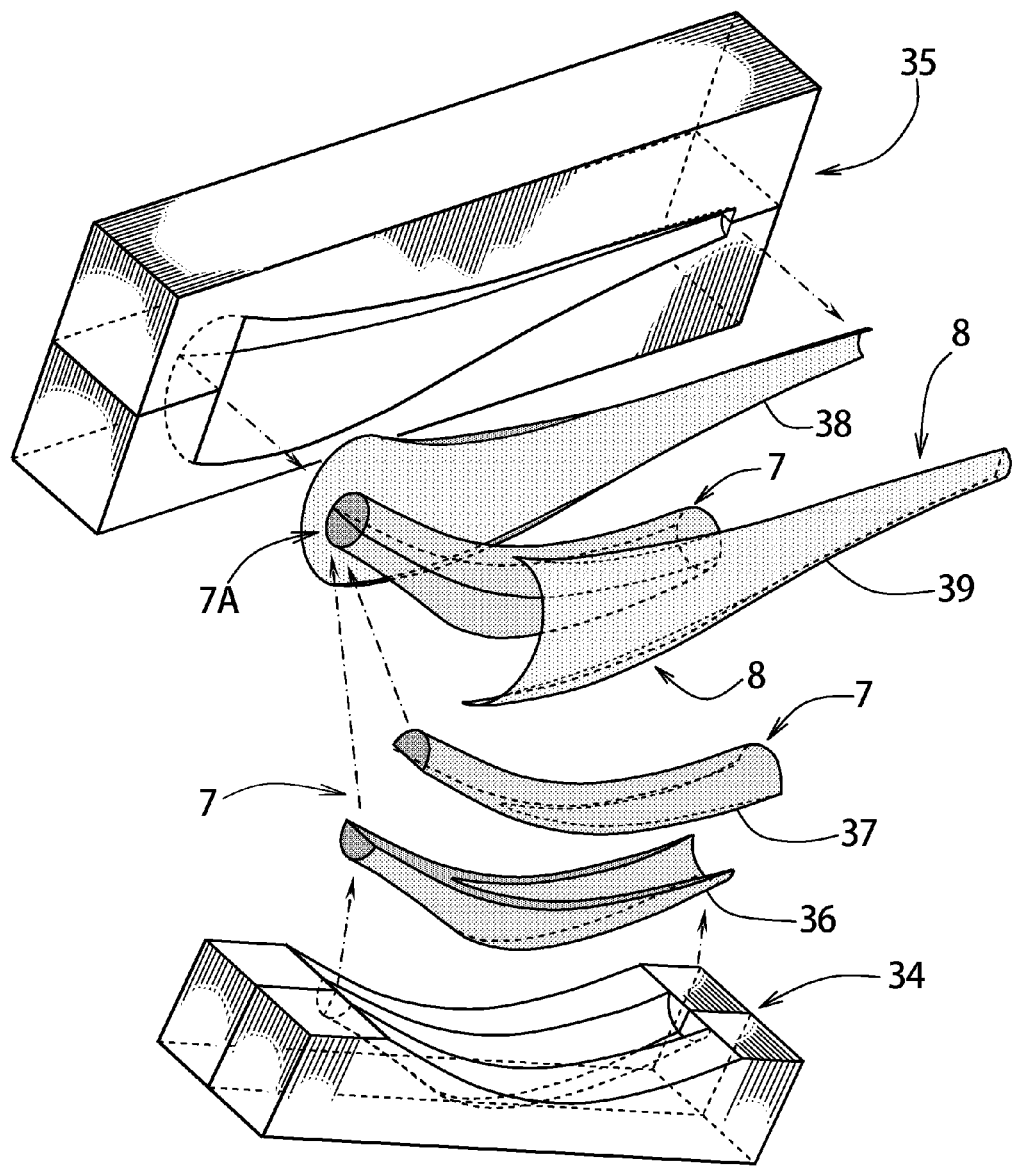
FIG. 7 is a dismantled perspective view of an example showing the process to form the parts of the stem.

The shapes of the inner construct 7 and the outer construct 8 forming the stems which are composite material moldings made of fiber reinforced plastics, are continuous circumferentially themselves, respectively, therefore, each of them can be formed like a column or a cylinder. However, it is more favorable to divide the construct into two halves along the parting surface including the longitudinal axis thereof, as shown in FIG. 7. The molds 34 and 35 are shown as one of a pair of molds, and each construct consists of two halves of 36 and 37 or 38 and 39 arranging the fibers in the direction as shown in FIG. 3 and FIG. 4 (*a*). The halves trimmed after the release from the molds for forming the shape of the individual half are united with each other by means of the finishing molds, not shown, for assembling into a complete construct. This is, the halves 36, 37 for the inner construct are met each other while the neck 7A is hold by a tool, not shown. The halves 38 and 39 for the outer construct are met each other so as to cover the halves of the inner construct 7. The finishing molds for assembling the stem are closed tightly after accommodating all of halves for constructs and a balloon, not shown, for stopping the advance of the adhesive filler mentioned before into the cavities (see reference numbers of 13 and 14 in FIG. 1).

Figure 8:
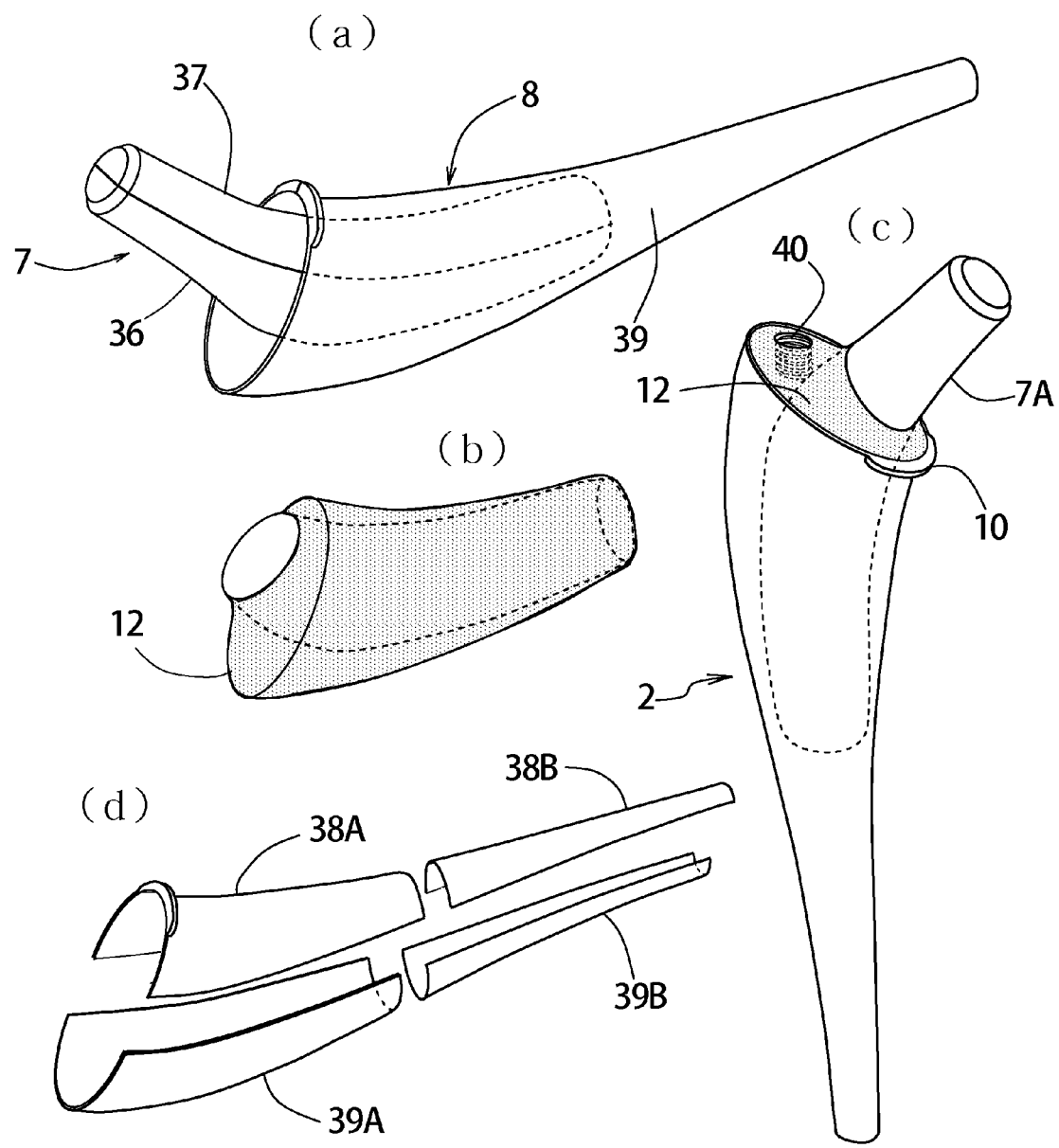
FIG. 8 shows the process to form the stem, (a) is a perspective view of the stem whose outer construct is surrounding the inner construct, (b) is a perspective view of the adhesive filler alone after being solidified, (c) is a perspective view of the final assembly of the stem provided with the screw insert, and (d) is a perspective view of the outer construct divided into four parts.

Thermoplastic resin or its compound is injected into the space between the inner construct 7 and the outer construct 8 shown in FIG. 8 (*a*), so that the resin spreads to even narrow spaces including the small clearances between the butted edges of halves for constructs in accordance with the principle of hydrostatic pressure. (*b*) of the figure shows the adhesive filler 12 alone after being solidified. (*c*) of the same shows the stem made of composite material with final outer shape as an assembly. It is favorable to give an insert 40 having a hole for engaging with a screw mentioned later to the top of the solidified adhesive filler 12.

Figure 9:
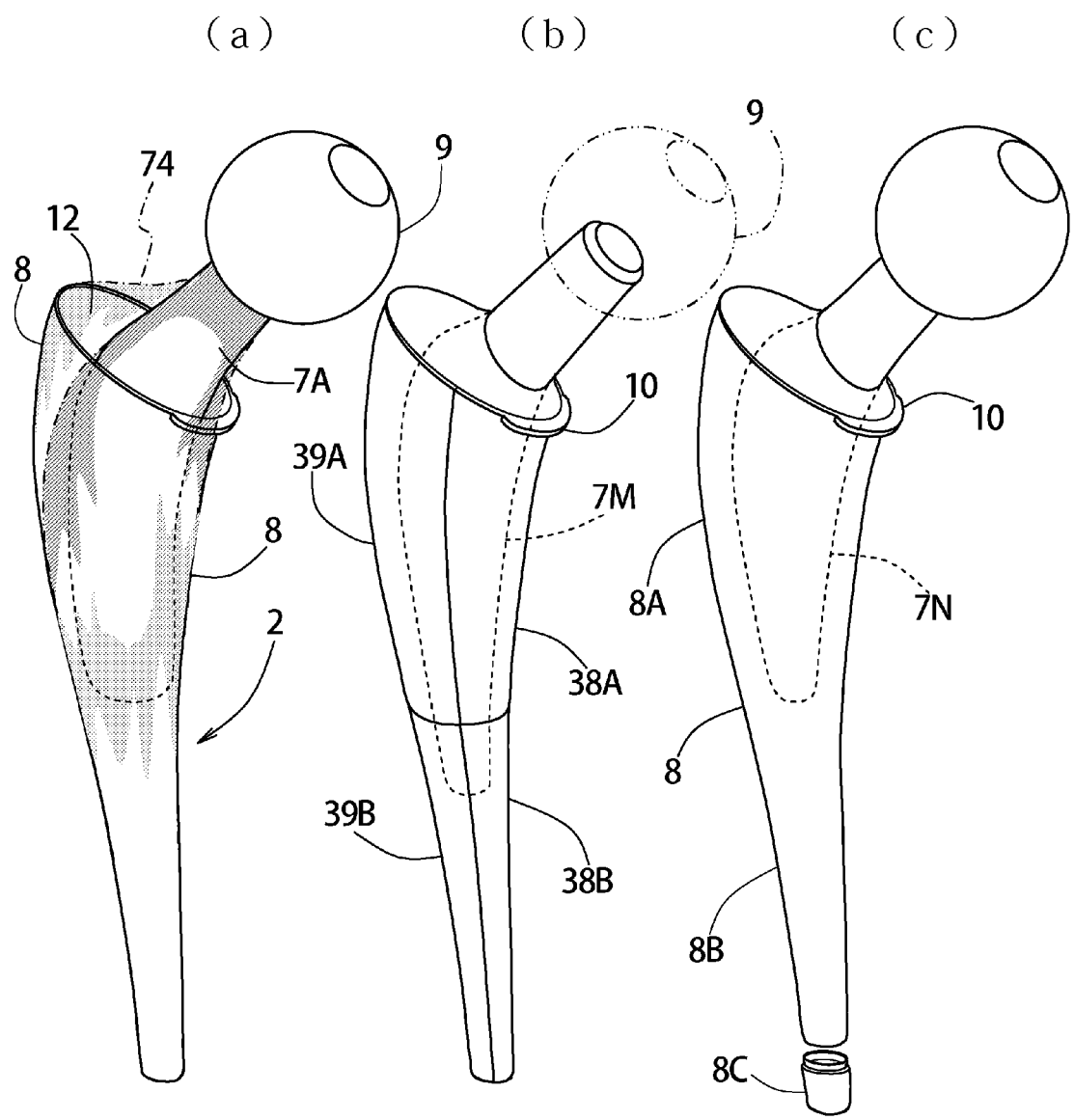
FIG. 9 shows a few examples of stems according to the present invention and a stem belonging to the prior art referred for the comparison.
Figure 14:
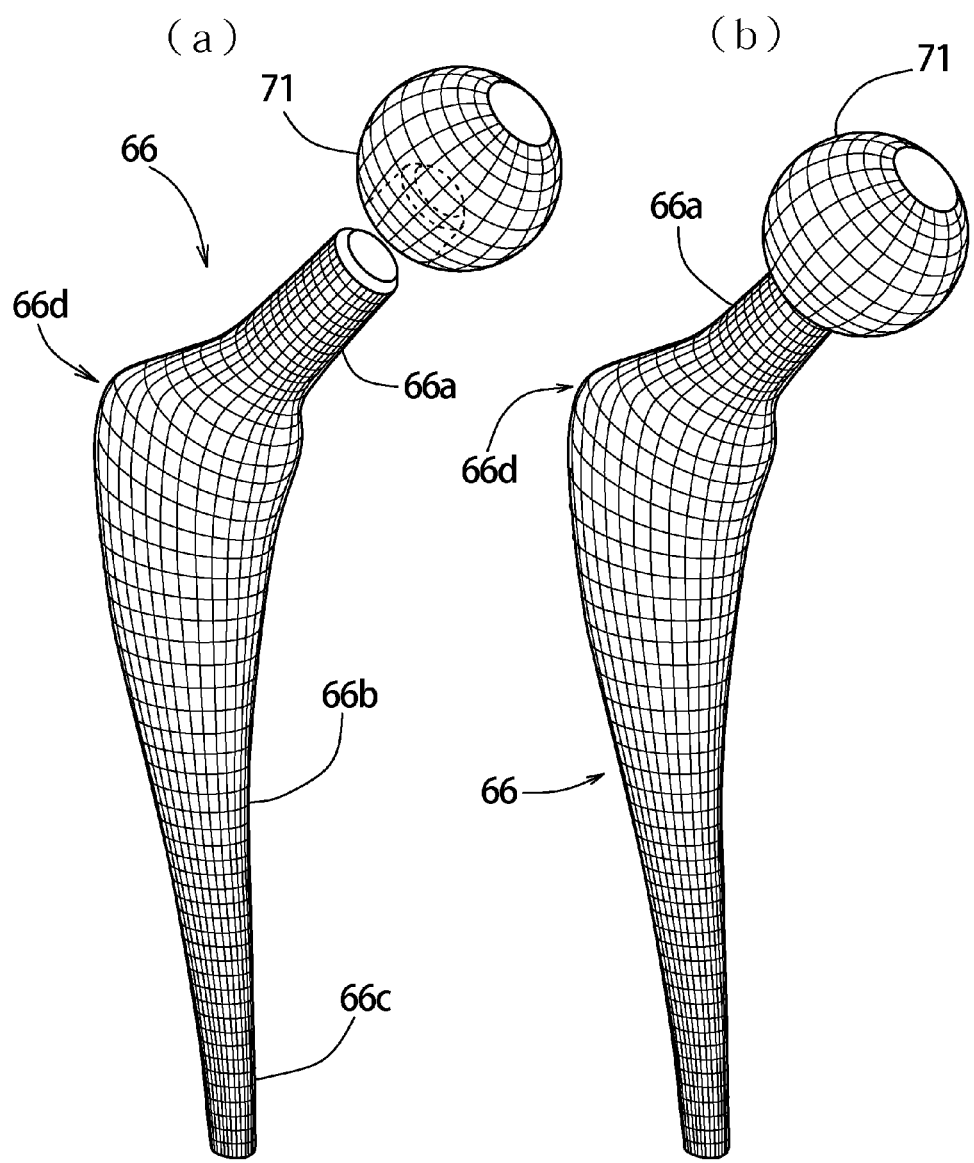
FIG. 14 is perspective views of the femoral prostheses where the conventional metallic stems are depicted in graphic arts.
Figure 16:
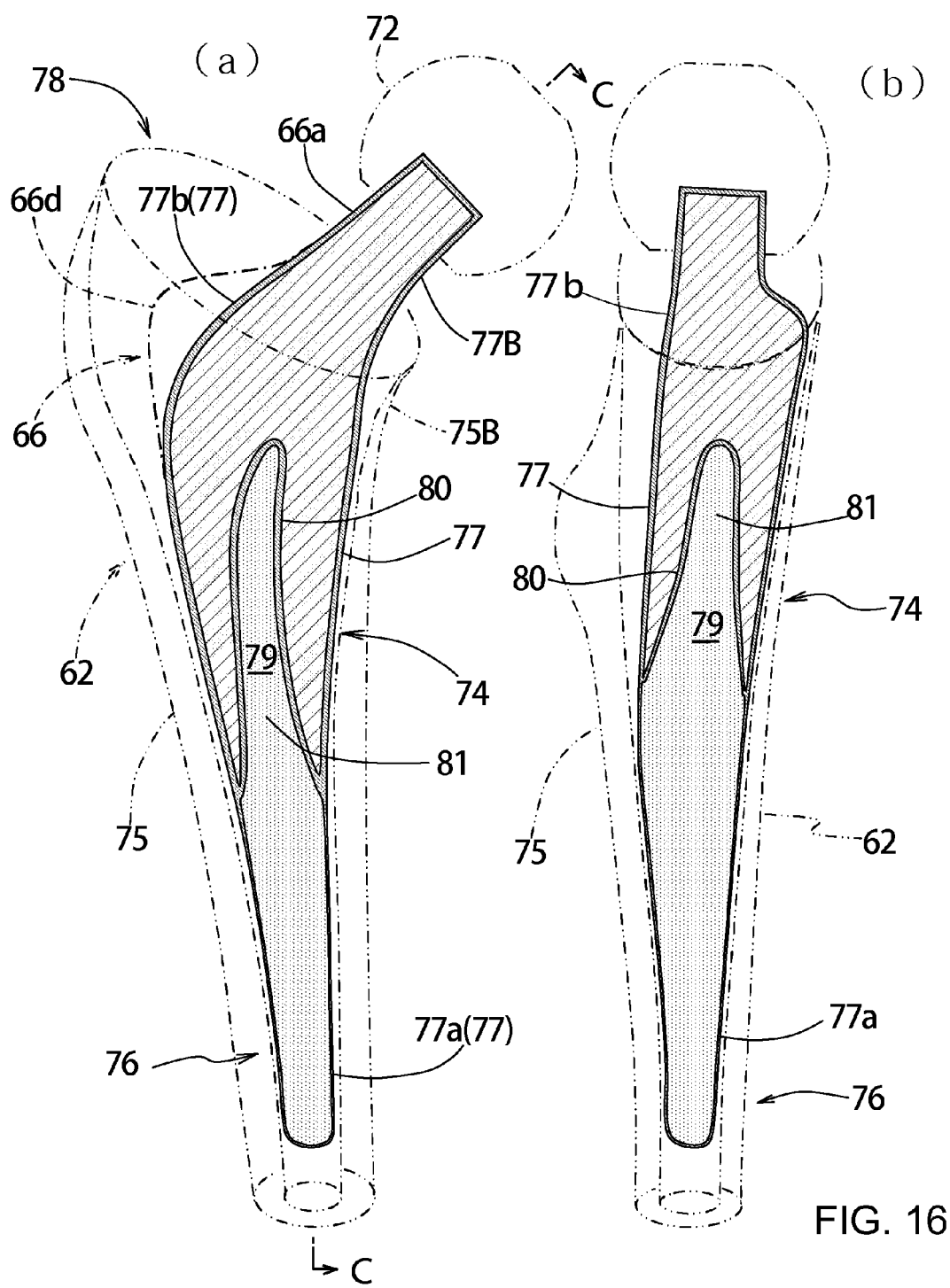
FIG. 16 is an example of the stem with varied rigidity belonging to prior art; (a) is a front view corresponding to that of the human body and (b) is a sectional view taking along lines C-C in (a) of the figure.

FIG. 9 (*a*) is a schematic view of the stem 2 made in this manner, which is overlapped with the stem 74 without the outer construct shown in FIG. 16. The shape of the stem 2 which contains the adhesive filler 12 inside the outer construct 8 substantially coincides with that of the stem 66 having a shoulder 66*d* shown in FIG. 14. It is obvious that the stem made of composite material having Fit and Fill around the epiphsis thereof being equivalent to that around the epiphsis of metallic stem can be made easily.

In the case mentioned above, one half of the outer construct 8 consists of one half of the outer body 8A and one half of the leg 8B, which are continuous with each other. However, one half of the bell mouth-shaped shell of the outer body may be made independently of one half of a conical leg as shown in FIG. 8 (*d*). The number of parts for the outer construct disposed in finishing molds becomes 4 of reference numbers 38A, 38B, 39A, 39B which are united with each other as shown in FIG. 9 (*b*) because the adhesive filler 12 can advance into the small clearances of the boundaries of four parts. In this example, the moldings 38B and 39B having a few plies can be favorably formed independently of the moldings 38A and 39A having a lot of plies.

In FIGS. 9 (*b*) and (*c*), the inner constructs of 7M and 7N have the different shapes from ones mentioned before. The diameter and the length of the individual construct is determined in consideration of the width of the load transmitting surface and the strength distribution of the femur, etc. FIG. 9 (*c*) is an example where a cap 8C working as a cover of the cavity formed in the leg is fixed on the distal end of the outer construct 8, so as to store a capsule or capsules for containing medicament for Bone-Growth mentioned after.

Process to implant the stem into the femur and to replace the stem is explained briefly hereinafter. The spongiosa in the femur is excised so as to form an undersized deep hollow 6 (see FIG. 1, wherein the deep hollow is drawn to be oversized for convenience.) by means of a medical rasp. The stem 2 whose neck 7A is engaged with the spherical head 9 is driven into the femur gradually under the computer monitoring of the position detected by a sensor (not shown) fixed to the insert 40 shown in FIG. 8 (c). When the hook 10 touches the cortical bone of medial side (see FIG. 1 (a)), the implanted depth and the rotational posture of the stem 2 are finely adjusted referring to the information of the position and the posture thereof calculated by a computer from the data detected. Since the shapes of the deep hollow 6 and the stem 2 have been already determined from the three dimensional CT graphics data taken before the operation, so that Fit and Fill can be obtained as high as possible. After the operation patients have to lie quietly in bed for Bone-Growth. Once the stem 2 is surely united with the femur, he can start practicing walking.

When the balance of the strength between the stem and the femur is lost due to aging and the like, the function of an artificial hip prosthesis deteriorates. It is important not to break the femur during the operation for replacing an artificial hip prosthesis. Since the inner construct 7 is provided with the cavity 13, it is easy to form a notch 41 and to remove the portion from the notch to the distal portion of the inner body from the femur by pushing the inner body in the direction of the arrow 42, as shown in FIG. 10 (a). Alternatively, the stem can be removed by pulling the clevis 44 which holds the pin 43 passing through the hole drilled into the neck 7A, as shown in (b) of the figure. Or, in the case that the insert 40 is provided with the stem as shown in (c), the stem can be removed gradually to hold the damages of the femur 1 at a minimum by striking the hitting block 47 in the direction of the arrow 48 with a hummer while gripping the handle 46 of a drawing bench 45 engaging the screw 45a with the inner screw of the insert. Of course, other operating and/or working processes may be applicable. The stem 2A in the figure is an example without a hook as a stopper hung on the opening edge of the deep hollow.

FIG. 11 (a) is an example of another stem 2, wherein a small open space 12a which is not filled with adhesive filler is formed inside the proximal end of medial side of the outer body 8A. When the bending moment acts on the stem 2 to press against the femur, not shown, due to the vertical load 49 acted on spherical head, the upper end 8a at the medial side of the outer body 8A may be deformed easily because of the absence of the adhesive filler 12 at the small open space as shown in the enlarged cross section surrounded by a circle. Even if the stem repeats such behavior many times, the damage of the outer body 8A can be avoided. In the case that a circular groove 12b including the small open space 12a is formed on the whole of top of the adhesive filler 12, the rigidity of the proximal end of the outer body 8A is decreased furthermore.

FIG. 11 (b) shows the leg 8B which stores medicament 50 for Bone-Growth in the cavity 14. In this case, the leg 8B is provided with holes 51 for passing the medicament through. The holes allow the medullary humor to flow into the cavity, and the mixture of the medullary humor with the medicament permeated through the semi-permeable membrane 51a can also flow out of the cavity through the holes. The mixture not only appears to the interface mentioned before but also advances to the outer surface of the intermediate portion 18 of the outer body 8A, contributing to Bone-Growth and the sterilization at the region where the load is charged. The jellified medicament for Bone-Growth may be either charged through the opening of the leg after the removal of a cap 8C or injected through the holes by the syringe. The cavity 13 of the inner body 7B increases the capacity for accommodating the medicament so as to keep the virtue of medicine for a certain period of time.

FIG. 11 (c) is an example of the stem with the leg 8B filled with thermoplastic resin 12A. This means that the distal portion of the outer construct 8 comes to be solid in some degree. The local deformation and wrinkles occurred in the case that the leg is filled with resin are much less than those occurred in the case of a hollow leg. The gradual deformation of the whole of leg 8B makes itself fit the medullary cavity preferably. The leg improved so as to keep the shape thereof can be also charged by the residual load which the outer body 8A could not transmit. The resin charged into the leg may be also the foam of the thermoplastic resin. The resin may be also charged into the cavity 13 of the inner body 7B so as to be continuous with the resin in the cavity of the leg. In any case, the elastic modulus of the resin charged into is much lower than that of the inner body 7B itself, so that the resin never changes the balance of rigidities of the outer construct 8 and the inner construct 7.

FIG. 11(c) shows the outer construct 8 with a shell of constant thickness, which is accomplished by decreasing the number of plies due to the use of fibers for reinforcement of different elastic modulus. Therefore, the outer construct 8 does not always have to be varied in thickness as shown in FIG. 3. It is important that the outer construct made of composite material has the rigidity of distribution suitable for the femur of patient.

As shown in FIG. 12(a), the distal end 7a of the inner body 7B may also contact the inner surface of the outer construct 8. In this case, the inner body should contact the outer body 8A at the portion with high rigidity, so that the influence of the back-up effect of the inner construct 7B on the outer construct can be remained very small. The shortening of the inner construct 7 enables shortening of the leg 8B which ought not to be charged with the influence of contact with the inner body 7B. The stem with a changeable structure comes to be also applicable to a patient with small build.

Figure 12:
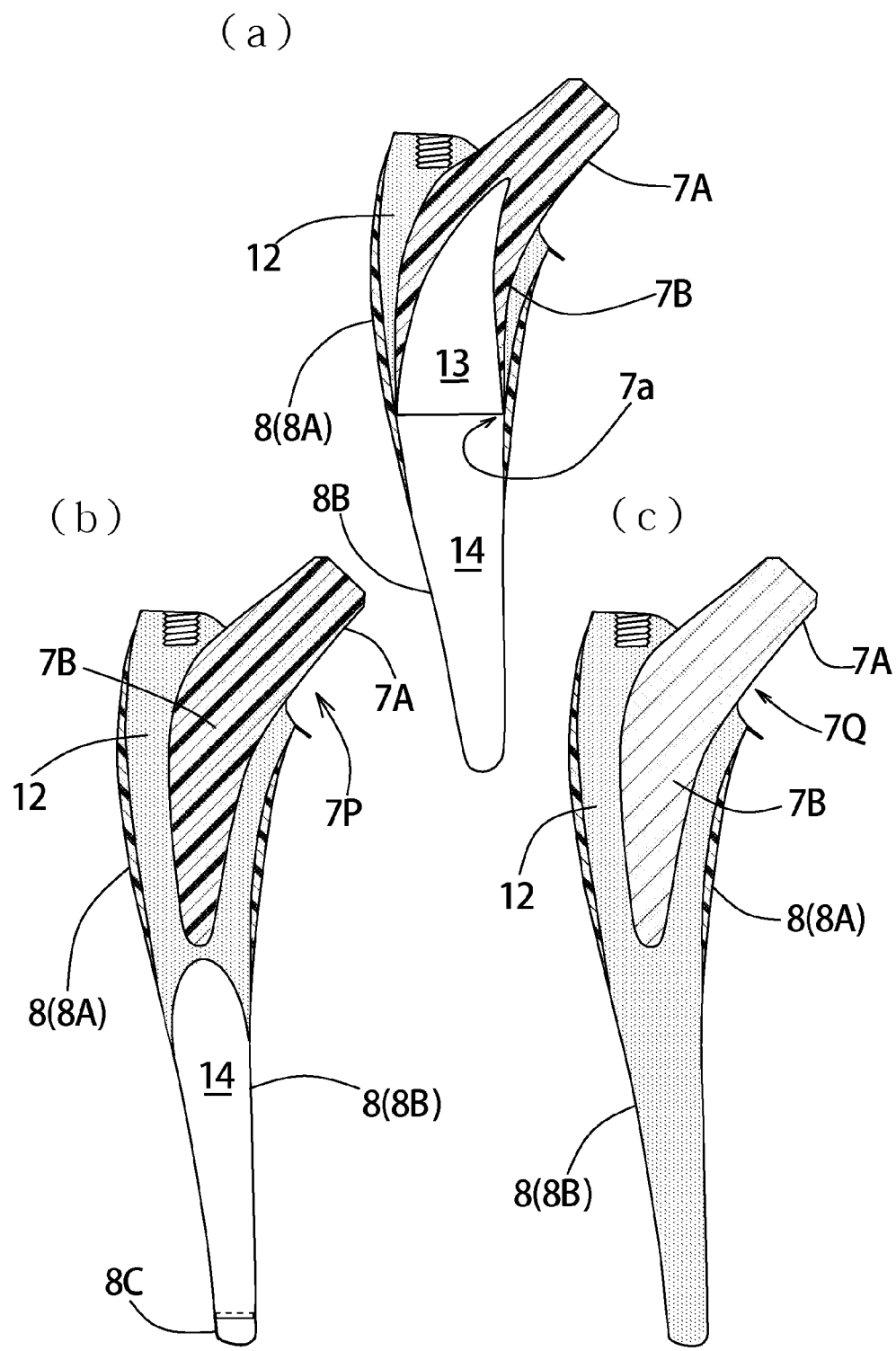
FIG. 12 shows other stems according to the present invention.
Figure 13:
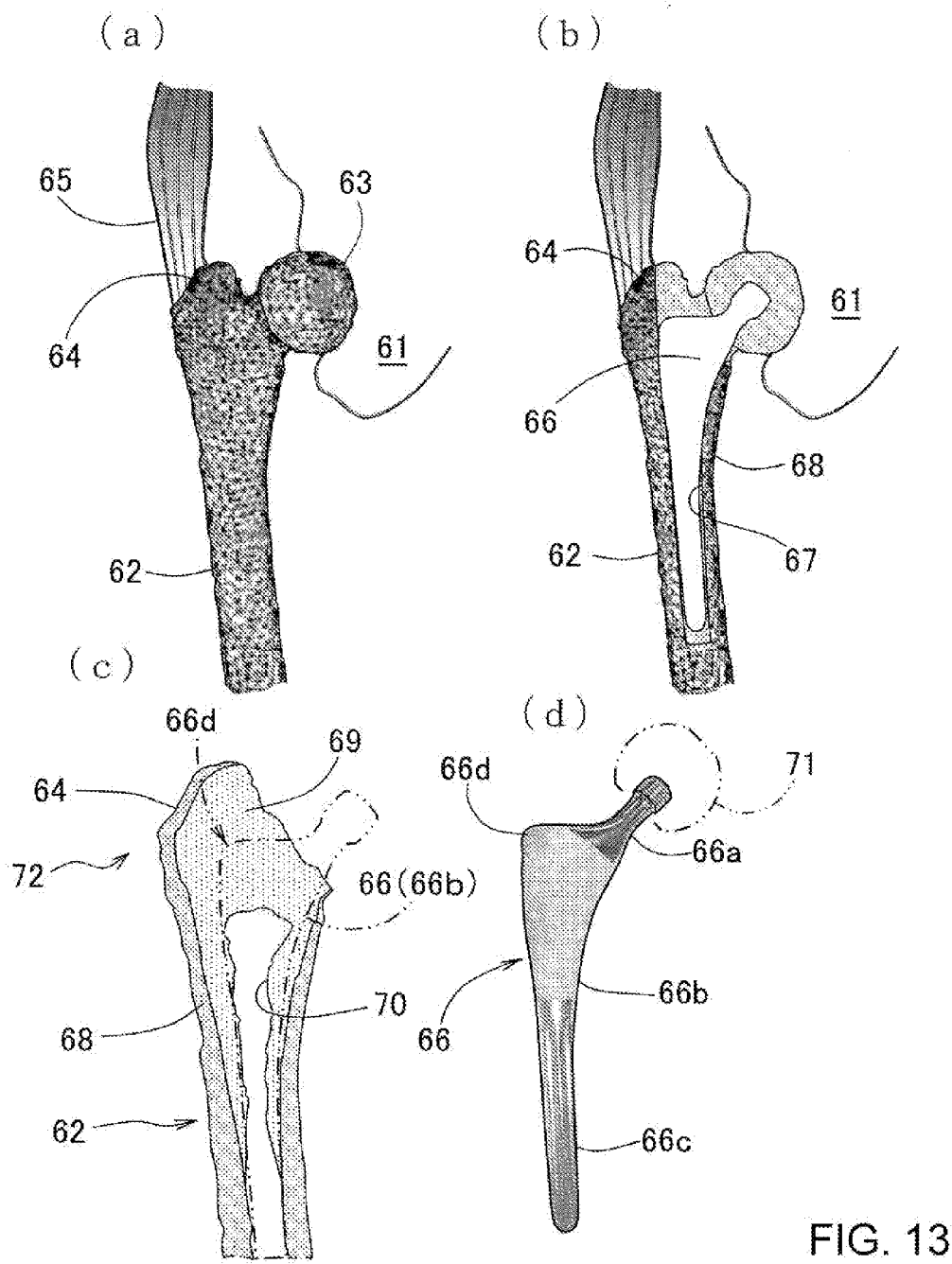
FIG. 13 is explanatory diagrams showing the process to implant the conventional metallic stem into the femur.

FIG. 12 (b) is an example of a stem where an inner construct is a composite material product 7P of a solid structure, which is different from the inner construct 7 of FIG. 1 in a respect that it does not have a cavity 13. This stem is usable as long as both the inner construct does not directly contact the inner surface of the outer construct 8 and the adhesive filler 12 is reasonably thick, for the rigidity and its distribution of the outer body 8A are not affected very much by those of the inner construct. Consequently, a cobalt alloy product or a titanium alloy product 7Q is applicable to the inner construct as shown in (c) of the figure. The adhesive filler 12 having a thicker layer gives the flexibility on the determination of the outer shape of the inner construct, so that the ready-made inner construct can be progressively developed. The promotion of the mass-productivity of the inner body facilitates lowering the whole of price of a hip joint of custom-made.

The stem according to the present invention as explained above in detail prevents the bone of the femur from being thinner and the density of bone from lowering, by keeping the load charged on the stem, especially, on the proximal portion where the bone activates under the appropriate load. Besides, eliminating of the looseness and Micro-Movement of the stem never generate the worn powder from the stem, so that Fit and Fill can be improved, in addition, Interfacial Separation and destruction of bone scarcely occur.

The weakness of the cortical bone at the medial side of a femur caused by the damage of caput and the removal of a part of cortical bone during excising the inside of the femur often make the strength of the femur lower. However, the stress concentration on the cortical bone at and around the portion weakened and/or removed is eliminated by adopting the present invention. This means that the artificial hip prosthesis stem is widely applicable to patients including ones suffering from osteoporosis. Because the rigidity can be decreased at even the epiphysis whose rigidity has been lowered no longer by reason of the existence of the neck and the unextendable cavity. The invention facilitates to make the stem which easily fits the deep hollow whose shape is obtained from the three dimensional CT graphics data of the femur and to control the pressure inside the molds because of the thin structure of the outer construct. As a result, the miniaturization and lightening of the mold will progress and the inexpensive and harmless stems will be able to be supplied to the market with the potential to be ready-made partially.

SYMBOLS 1, 1A: femur,
1a: cortical bone,
2, 2A: stem,
3: greater trochanter,
4: epiphysis,
5: diaphysis,
6: deep hollow,
7: inner construct,
7A: neck,
7B, 7M, 7N: inner body,
7P: inner construct made of composite material product of a solid structure,
7Q: inner construct made of titanium alloy,
7a: distal end,
8: outer construct,
8A: outer body,
8B: leg,
8C: cap,
9: spherical head,
10: hook,
11: medullary cavity,
12, 12A: adhesive filler,
12a: small open space,
12b: circular groove,
13, 14: cavity,
15: single-dotted chain lines (torsional rigidity of femur),
16: double-dotted chain lines,
17: solid lines (torsional rigidity of stem),
18: intermediate portion,
19: broken line,
20: thin solid line (torsional shearing stress occurred on the interface of metallic stem),
21: longitudinal axis,
22: woven cloth arranged at an angle of approximate 45 degrees,
23: woven cloth arranged at angles of 0/90 degrees to the longitudinal axis,
24: uni-directional fiber,
25: most outer layer,
26: most inner layer,
27: middle layer,
28: tomograms,
30: image, graphics,
31: distribution of rigidity,
32: concave grooves,
33: particle of hydroxyapatite,
34,35: mold,
36~39, 38A, 38B, 39A, 39B: halves of construct,
40: insert,
41: notch,
42: arrow,
43: pin,
44: clevis,
45: drawing bench,
45a: screw,
46: handle,
47: hitting block,
48: arrow,
49: vertical load,
50: medicament for Bone-Growth,
51: holes,
51a: semipermeable membrane,
61: pelvis,
62: femur,
62A: outer cylinder,
63: caput,
64: greater trochanter,
65: gluteus medius,
65B: cortical bone,
66: metallic stem (short rod),
66A: inner cylinder,
66a: neck,
66b: body part,
66c: leg, 66d: shoulder,
67: deep hollow,
68: cortical bone,
69: spongiosa,
70: medullary cavity,
71: spherical head,
72: epiphysis,
73: interface,
73e: end,
74: composite material stem,
75: cortical bone,
75B: cortical bone,
76: diaphysis,
77,77B,77a,77b: epidermis,
78: epiphysis,
79: cavity,
80: inner epidermis,
81: foaming resin.

The invention claimed is:

1. An artificial cement-less hip prosthesis stem which is adapted to be implanted into a deep hollow extending from an epiphysis to a diaphysis of a femur so as not to pass through a greater trochanter thereof, and being adapted to gradually be united with the femur by bone growth, comprising;

an inner construct having both a neck to be engaged with a spherical head which works as a joint in cooperation with a socket adapted to be fixed to a pelvis and an inner body to be reacted with a load transmitted from the neck, an outer construct made of fiber reinforced plastics having both an outer body which is bell mouth-shaped and adapted to open toward the epiphysis so as to surround said inner body which is combined with the outer body by an adhesive filler filled in a space between the outer body and the inner body and a leg adapted to extend toward a medullary cavity, for transmitting a load acting on a hip joint to the femur, wherein said inner body does not directly contact an inner surface of the outer construct, and torsional rigidity given to a proximal end and a distal end of said outer body and the leg is regulated to be lower than a torsional rigidity of an intermediate portion of said outer body, resulting in transmitting the load distributed collectively on an intermediate portion to a proximal portion of the femur as uniformly as possible.

2. An artificial cement-less hip prosthesis stem according to claim 1, wherein said outer construct is made from inorganic fiber reinforced plastics, including a matrix composed of a thermoplastic resin.

3. An artificial cement-less hip prosthesis stem according to claim 2 wherein the thermoplastic resin is made from polyether ether ketone.

4. An artificial cement-less hip prosthesis stem according to claim 1, wherein said adhesive filler filled inside the outer body is either a thermoplastic resin, or a mixture containing chopped fiber mixed with the thermoplastic resin.

5. An artificial cement-less hip prosthesis stem according to claim 1, wherein the torsional rigidity given to said outer body except the intermediate portion is regulated to be lower than a torsional rigidity of the bone around the deep hollow corresponding thereto, and the torsional rigidity given to the intermediate portion is regulated to be higher than the torsional rigidity of the bone around the deep hollow corresponding to the intermediate portion.

6. An artificial cement-less hip prosthesis stem according to claim 1, wherein a woven cloth having fibers arranged at an angle of approximately 45degrees relative to a longitudinal axis of said artificial cement-less hip prosthesis stem is overlaid over a whole surface of said outer construct, and a woven cloth whose fibers are arranged at an angle of other degrees is overlaid only over a part of the surface.

7. An artificial cement-less hip prosthesis stem according to claim 1, wherein said leg adapted to extend toward the medullary cavity in the diaphysis has a cavity opening at a proximal end thereof.

8. An artificial cement-less hip prosthesis stem according to claim 7, wherein said leg is provided with holes for passing therethrough a medicament adapted to be stored therein for promoting bone growth.

9. An artificial cement-less hip prosthesis stem according to claim 1, wherein the inner construct is made of fiber reinforced plastics, and woven cloths having fibers arranged at angles of approximate both 45 and 0/90 degrees relative to a longitudinal axis of the artificial cement-less hip prosthesis stem are overlaid over a whole surface of said inner construct.

10. An artificial cement-less hip prosthesis stem according to claim 1, wherein said inner construct has a shape gradually changed from the neck toward a distal portion thereof without having a shoulder adapted to project toward the greater trochanter.

11. An artificial cement-less hip prosthesis stem according to claim 1, wherein the adhesive filler is not filled inside a proximal end of a medial side of the outer body.

12. An artificial cement-less hip prosthesis stem according to claim 1, wherein a thermoplastic resin or a thermoplastic foam is charged into said leg so that a distal portion of the outer construct becomes solid.

13. An artificial cement-less hip prosthesis stem according to claim 1, wherein fine concave grooves are formed on the outer surface of said outer body.

14. An artificial cement-less hip prosthesis stem according to claim 1, wherein the outer surface of said outer body is coated with hydroxyapatite.

15. An artificial cement-less hip prosthesis stem according to claim 1, wherein a proximal end of a medial side of said outer body includes a hook adapted to be hung on an opening edge of said deep hollow.

16. An artificial cement-less hip prosthesis stem according to claim 1, wherein both said outer construct and inner construct are divided into two halves which mate together to form said outer construct and said inner construct.

17. An artificial cement-less hip prosthesis stem according to claim 1, wherein said inner construct is made of cobalt alloy or titanium alloy.

18. An artificial cement-less hip prosthesis stem according to claim 1, wherein fine concave grooves are formed on the intermediate portion of the outer surface of said outer body.

19. An artificial cement-less hip prosthesis stem which is adapted to be implanted into a deep hollow extending from an epiphysis to a diaphysis of a femur so as not to pass through a greater trochanter thereof, and being adapted to gradually be united with the femur by bone growth, comprising;
   an inner construct having both a neck to be engaged with a spherical head which works as a joint in cooperation with a socket adapted to be fixed to a pelvis and an inner body to be reacted with a load transmitted from the neck,
   an outer construct made of fiber reinforced plastics having both an outer body which is adapted to be bell mouth-shaped toward the epiphysis so as to surround said inner body which is combined with the outer body by an adhesive filler filled in a space between the outer body and the inner body and a leg adapted to extend toward a medullary cavity, for transmitting a load acting on a hip joint to the femur, and
   torsional rigidity given to a proximal end and a distal end of said outer body and the leg is regulated to be lower than a torsional rigidity of an intermediate portion of said outer body, resulting in transmitting the load distributed collectively on an intermediate portion to a proximal portion of the femur as uniformly as possible, and,
   wherein said inner body has a cavity formed inside, the cavity having a cross-section which increases towards a distal portion of said inner body.

20. An artificial cement-less hip prosthesis stem according to claim 19 wherein the distal end of said inner body contacts the inner surface of the outer construct.

* * * * *